US011875365B2

(12) United States Patent
Sloat et al.

(10) Patent No.: US 11,875,365 B2
(45) Date of Patent: Jan. 16, 2024

(54) USER EXPERIENCE COMPUTING SYSTEM FOR GATHERING AND PROCESSING USER EXPERIENCE INFORMATION

(71) Applicant: Fresenius Medical Care Holdings, Inc., Waltham, MA (US)

(72) Inventors: Daniel L. Sloat, Lexington, MA (US); Beth Kun, Lexington, MA (US); Brittany R. Aube, Lexington, MA (US); Benjamin N. Davies, Lexington, MA (US); Derek Merrikin, Lexington, MA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 203 days.

(21) Appl. No.: 17/078,989

(22) Filed: Oct. 23, 2020

(65) Prior Publication Data

US 2022/0129917 A1    Apr. 28, 2022

(51) Int. Cl.
*G06Q 30/0201* (2023.01)
*G06F 16/28* (2019.01)
(Continued)

(52) U.S. Cl.
CPC ....... *G06Q 30/0201* (2013.01); *G06F 16/258* (2019.01); *G06F 16/285* (2019.01);
(Continued)

(58) Field of Classification Search
USPC ...................................................... 705/7.29
See application file for complete search history.

(56) References Cited

U.S. PATENT DOCUMENTS 8,323,503 B2    12/2012    Levin et al.
8,543,420 B2     9/2013    Darby et al.
(Continued)

FOREIGN PATENT DOCUMENTS

WO    WO 2017/013494 A2    1/2017

OTHER PUBLICATIONS

Allam et al., Patient Similarity Analysis with Longitudinal Health Data, May 14, 2020 (Year: 2020).*
(Continued)

*Primary Examiner* — Brian M Epstein
*Assistant Examiner* — Allison M Robinson
(74) *Attorney, Agent, or Firm* — Leydig, Voit & Mayer, Ltd.

(57) ABSTRACT

Enterprise organizations may use observational data to gather information about user experiences with their products and tools. For instance, patients with kidney failure may undergo dialysis treatment in order to remove toxins and excess fluids from their blood. The dialysis treatment may be performed at a hospital or clinic, or in a user's home, and the enterprise organization may use gathered information to gain understanding of user experiences with their dialysis machines and services. A user experience computing system gathers and processes user experience information from across the enterprise organization. Using stored observation data (e.g., surveys, studies etc.) in its smallest common form, the computing system may use this data as building blocks for creating more complex data objects (e.g. journey matrices and/or empathy gardens) using inputs from multiple different sources, and to facilitate presenting this information in an effective and empathetic way to product developers.

14 Claims, 10 Drawing Sheets

(51) Int. Cl.
  *G06F 16/25* (2019.01)
  *G06Q 10/067* (2023.01)
  *G06N 20/00* (2019.01)
  *G16H 20/40* (2018.01)
  *G16H 40/20* (2018.01)
  *G16H 10/20* (2018.01)
  *G06F 40/20* (2020.01)
  *A61M 1/14* (2006.01)

(52) U.S. Cl.
  CPC ........... *G06N 20/00* (2019.01); *G06Q 10/067* (2013.01); *A61M 1/14* (2013.01); *G06F 40/20* (2020.01); *G16H 10/20* (2018.01); *G16H 20/40* (2018.01); *G16H 40/20* (2018.01)

(56) References Cited

U.S. PATENT DOCUMENTS

| | | | |
|---|---|---|---|
| 8,632,485 | B2 | 1/2014 | Schlaeper et al. |
| 8,698,741 | B1 | 4/2014 | Wang et al. |
| 8,924,458 | B2 | 12/2014 | Levin et al. |
| 9,514,283 | B2 | 12/2016 | Childers et al. |
| 9,839,735 | B2 | 12/2017 | Tanenbaum et al. |
| 10,288,881 | B2 | 5/2019 | Christensen |
| 10,441,696 | B2 | 10/2019 | Tanenbaum et al. |
| 11,031,128 | B2 | 6/2021 | Plahey et al. |
| 2008/0201280 | A1* | 8/2008 | Martin ............... G06N 20/00 706/45 |
| 2012/0101860 | A1 | 4/2012 | Ezzat |
| 2013/0172806 | A1 | 7/2013 | Griessmann et al. |
| 2014/0257003 | A1 | 9/2014 | Tschirschwitz et al. |
| 2015/0012467 | A1 | 1/2015 | Greystoke et al. |
| 2016/0206800 | A1 | 7/2016 | Tanenbaum et al. |
| 2017/0048585 | A1 | 2/2017 | Dong et al. |
| 2017/0168688 | A1 | 6/2017 | Yuds |
| 2017/0293919 | A1* | 10/2017 | Li ............... G06Q 30/0201 |
| 2018/0336183 | A1* | 11/2018 | Lee ............... G06N 5/022 |
| 2019/0209764 | A1 | 7/2019 | Buraczenski et al. |
| 2019/0327584 | A1 | 10/2019 | Plahey et al. |
| 2019/0377818 | A1* | 12/2019 | Andritsos ........... G06F 16/2465 |
| 2020/0226479 | A1* | 7/2020 | Germanakos ........... G06F 40/30 |
| 2020/0394026 | A1* | 12/2020 | Huang ............... G06N 20/00 |
| 2020/0401571 | A1* | 12/2020 | Poliakova ............. G06N 5/022 |
| 2021/0093764 | A1 | 4/2021 | Merics et al. |
| 2021/0406934 | A1* | 12/2021 | Arias ............... G06Q 30/0203 |

OTHER PUBLICATIONS

International Patent Application No. PCT/US2021/054290, International Search Report (dated Jan. 28, 2022).

\* cited by examiner

USER EXPERIENCE COMPUTING SYSTEM FOR GATHERING AND PROCESSING USER EXPERIENCE INFORMATION

BACKGROUND

Enterprise organizations may perform studies or generate surveys to gather more information about user experiences with their products and tools. For instance, patients with kidney failure or partial kidney failure typically undergo dialysis treatment in order to remove toxins and excess fluids from their blood. The dialysis treatment may be performed at a hospital or clinic, or at a user's home rather than in a hospital setting, and the enterprise organization may perform studies to gain understanding of user experiences with their dialysis machines and services. The enterprise organization may perform numerous different studies, surveys, and so on regarding the dialysis machine and/or other products or tools associated with the enterprise organization. After each study is completed, the results may be published and used, but the underlying data may be discarded and/or not used again. This underlying data may hold important information regarding the user and the enterprise organization may seek to use it in the future.

However, the underlying data may be in different data formats including non-standardized data formats, which may make it difficult to consolidate and gain insights into the user experiences from these studies. For instance, it may be difficult to determine insights, similarities, and differences between numerous studies conducted by the enterprise organization if these studies use different data formats. Furthermore, without a process to standardize this information, it may be difficult for the enterprise organization to maintain these studies and leverage previous user experiences in order to provide better user experiences in the future. Additionally, without standardized information, it is difficult for the enterprise organization to effectively present or distribute this information to audiences (e.g., internal audiences) that are developing and improving products and services of the enterprise organization. Accordingly, there remains a technical need for converting studies that are in non-standardized data formats into standardized data formats so they can be used to provide better user experiences and facilitate the development of improvements to user experiences within an enterprise organization.

SUMMARY

An embodiment of the disclosure provides a method for using a user experience (UX) system. The method comprises: receiving, by a UX computing system, observation data in a plurality of non-standardized data formats, wherein the observation data comprises user experiences associated with a plurality of actors interacting with a product or service associated with an enterprise organization; converting, by the UX computing system, the observation data from the plurality of non-standardized data formats into one or more standardized data formats; receiving, by the UX computing system, a request associated with an actor model, wherein the actor model represents a subset of the plurality of actors; generating, by the UX computing system, a journey matrix for the requested actor model based on the converted observation data, wherein the journey matrix indicates a plurality of sequential moments describing the actor model interacting with the product or service; and causing display of the journey matrix.

In some instances, the observation data comprises unstructured observation data and structured observation data, and the converting the observation data into the one or more standardized data formats comprises converting both the unstructured observation data and the structured observation data into a same standardized data format.

In some examples, the converting the observation data into the one or more standardized data formats is based on using a user hub information architecture, the user hub information architecture comprises a plurality of classification identifiers.

In some variations, the converting the observation data into one or more standardized data formats based on using the user hub information architecture comprises: continuously breaking down the observation data into smaller chunks of data; and assigning a classification identifier from the plurality of classification identifiers at each stage of the break down of the observation data.

In some instances, the plurality of classification identifiers comprises a moment classification identifier associated with a plurality of moment data elements and a story classification identifier associated with a plurality of story data elements, and the converting the observation data into the one or more standardized data formats comprises: breaking down the observation data into the plurality of story data elements, wherein each of the plurality of story data elements is associated with a user experience of an actor interacting with the product or service at a plurality of different instances in time; and breaking down each of the plurality of story data elements into the plurality of moment data elements, wherein each of the plurality of moment data elements is associated with a plurality of variables at a particular instance in time from the plurality of different instances in time.

In some examples, the breaking down the observation data into the plurality of story data elements is based on first operator input associated with an operator, and the breaking down each of the plurality of story data elements into the plurality of moment data elements is based on second operator input associated with the operator.

In some variations, the generating the journey matrix for the requested actor model based on the converted observation data comprises: selecting, based on a taxonomy database, a subset of the plurality of moment data elements to include into the journey matrix, wherein the subset of the plurality of moment data elements is associated with the subset of the plurality of actors; and generating the journey matrix for the requested actor model by incorporating each of the subset of the plurality of moment data elements sequentially one after another based on an average temporal order for each of the subset of the plurality of moment data elements.

In some instances, the selecting the subset of the plurality of moment data elements is based on operator input associated with an operator.

In some examples, the method further comprises: categorizing the plurality of moment data elements into one or more categories of moments based on the taxonomy database, and wherein selecting the subset of the plurality of moment data elements is based on a number of the plurality of moment data elements within the one or more categories exceeding a threshold.

In some variations, the method further comprises: generating the actor model based on the request and the converted observation data, wherein generating the journey matrix is based on the generated actor model.

In some instances, the generating the actor model is based on: calculating an n-dimensional distance between a plurality of actors identified in the observation data; and clustering a subset of the plurality of actors together based on the request and using a clustering algorithm.

In some examples, the method further comprises: generating an empathy garden based on the journey matrix, wherein the empathy garden comprises the journey matrix and information associated with a moment data element from the journey matrix; and providing the empathy garden and the journey matrix to a second device.

Another embodiment of the disclosure provides system including a user experience (UX) computing system comprising: one or more processors; and a non-transitory computer-readable medium having processor-executable instructions stored thereon, wherein the processor-executable instructions, when executed by the one or more processors, facilitate: receiving observation data in a plurality of non-standardized data formats, wherein the observation data comprises user experiences associated with a plurality of actors interacting with a product or service associated with an enterprise organization; converting the observation data from the plurality of non-standardized data formats into one or more standardized data formats; receiving a request associated with an actor model, wherein the actor model represents a subset of the plurality of actors; generating a journey matrix for the requested actor model based on the converted observation data, wherein the journey matrix indicates a plurality of sequential moments describing the actor model interacting with the product or service; and causing display of the journey matrix.

In some instances, the observation data comprises unstructured observation data and structured observation data, and the converting the observation data into the one or more standardized data formats comprises converting both the unstructured observation data and the structured observation data into a same standardized data format.

In some examples, the converting the observation data into the one or more standardized data formats is based on using a user hub information architecture, the user hub information architecture comprises a plurality of classification identifiers.

In some variations, the converting the observation data into one or more standardized data formats based on using the user hub information architecture comprises: continuously breaking down the observation data into smaller chunks of data; and assigning a classification identifier from the plurality of classification identifiers at each stage of the break down of the observation data.

In some instances, the plurality of classification identifiers comprises a moment classification identifier associated with a plurality of moment data elements and a story classification identifier associated with a plurality of story data elements, and the converting the observation data into the one or more standardized data formats comprises: breaking down the observation data into the plurality of story data elements, wherein each of the plurality of story data elements is associated with a user experience of an actor interacting with the product or service at a plurality of different instances in time; and breaking down each of the plurality of story data elements into the plurality of moment data elements, wherein each of the plurality of moment data elements is associated with a plurality of variables at a particular instance in time from the plurality of different instances in time.

In some examples, the processor-execution instructions, when executed, further facilitate: generating the actor model based on the request and the converted observation data, wherein generating the journey matrix is based on the generated actor model.

In some variations, the generating the actor model is based on: calculating an n-dimensional distance between a plurality of actors identified in the observation data; and clustering a subset of the plurality of actors together based on the request and using a clustering algorithm.

Another embodiment of the disclosure provides a non-transitory computer-readable medium having processor-executable instructions stored thereon, wherein the processor-executable instructions, when executed by the one or more processors, facilitate: receiving observation data in a plurality of non-standardized data formats, wherein the observation data comprises user experiences associated with a plurality of actors interacting with a product or service associated with an enterprise organization; converting the observation data from the plurality of non-standardized data formats into one or more standardized data formats; receiving a request associated with an actor model, wherein the actor model represents a subset of the plurality of actors; generating a journey matrix for the requested actor model based on the converted observation data, wherein the journey matrix indicates a plurality of sequential moments describing the actor model interacting with the product or service; and causing display of the journey matrix.

DETAILED DESCRIPTION

Figure 1:
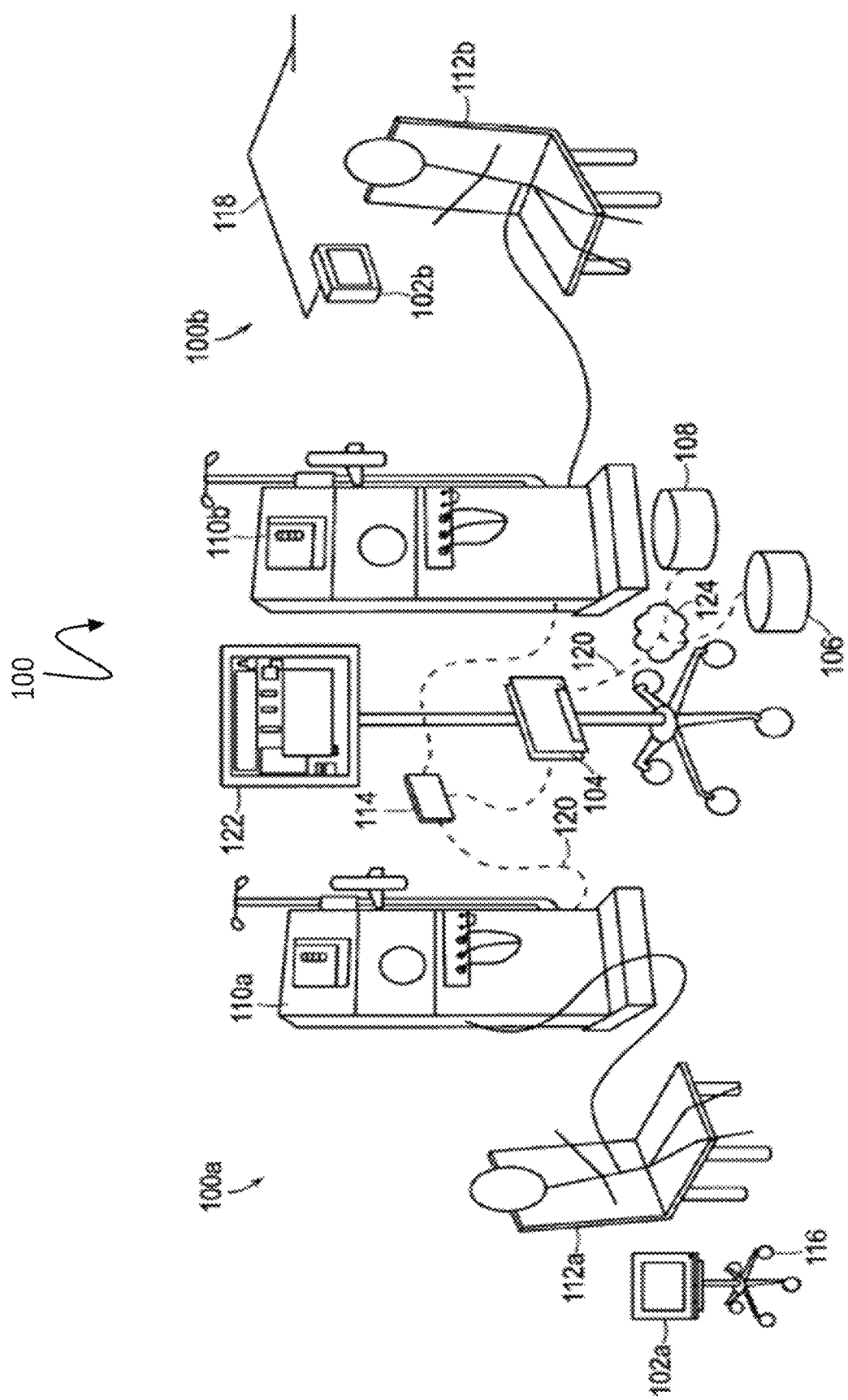
FIG. 1 is a schematic illustration showing an example user experience environment in a medical treatment context for which the system described herein may be utilized.

Examples of the presented application will now be described more fully hereinafter with reference to the accompanying FIGS., in which some, but not all, examples of the application are shown. Indeed, the application may be exemplified in different forms and should not be construed as limited to the examples set forth herein; rather, these examples are provided so that the application will satisfy applicable legal requirements. Where possible, any terms expressed in the singular form herein are meant to also include the plural form and vice versa, unless explicitly stated otherwise. Also, as used herein, the term "a" and/or "an" shall mean "one or more" even though the phrase "one or more" is also used herein. Furthermore, when it is said herein that something is "based on" something else, it may be based on one or more other things as well. In other words, unless expressly indicated otherwise, as used herein "based on" means "based at least in part on" or "based at least partially on".

As will be described in further detail below, a user experience (UX) computing system may gather user journey information, including users at home and in clinic, and including users who are patients, caregivers, technicians and/or clinicians, from across an enterprise organization. Based on this information, the UX computing system may determine "moments that matter." These moments may be particular experiences or instances in time that have high emotional scores that happen with regularity across the user population. Such moments may have feasible opportunities for spinning off solutions to either build on what is/has been successful or be used as improvement opportunities for the enterprise organization. For example, each user (e.g., actor) may have their own story within an overall story. For instance, when a patient is undergoing dialysis treatment, the patient will have a story to tell about the treatment. But, additionally, the clinician, nurse, caretaker, family member, physician and/or others may also have their own stories to tell. Each of these people within the story may be defined herein as a user or actor within the story. Furthermore, within each story, there may be multiple moments. A moment is a collection of variables that describe the happenings and context for one slice of time in the story and may be related to one or more actors. This may include information such as location, other actors that were present, products or devices that were used or present at the time, conversations that occurred or was said, events that occurred, and feelings that actors may have had at the time. For instance, in one such example, a moment within a story may be, "They were at home with their care partner. The dialysis machine was giving them an alarm that they could not clear. They were frustrated and scared." This moment may be followed by another moment within the same story that described the next set of events within a chain. For example, the next moment may include that the issue was resolved and the users felt a sense of relief and gratitude.

In some variations, a moment may be an important or recurring moment (e.g., a moment that matters). For example, a moment may be a moment that matters when it happens frequently, has significant emotional intensity, and/or is of the nature that may be used by the UX computing system to assist in resolving or supporting that type of moment in the future. For instance, within a study, multiple actors may be interviewed. Many of these actors may discuss a product that they might not like using in their treatments. This moment of using the product may have occurred many times across the study and may further be associated with a strong negative emotional score. Accordingly, the UX computing system may classify this moment as a moment that matters (e.g., based on the number of moments exceeding a threshold, based on operator input, and/or based on a high negative emotional score). By classifying moments as moments that matter, a researcher or another operator of the UX computing system may be able to identify important moments that may be used to benefi-cially impact the product, device, treatment, and additional goods or services provided by the enterprise organization.

Among other technical advantages and by using the UX computing system to gather user journey information, the UX computing system may be able to better categorize and/or capture the human dimensions and aspects such as feelings within a study. This may permit the captured information to be more distinct as well as introducing a new means to quantify humanistic data. For example, traditionally, feelings of actors within a study may be difficult to identify and define. However, these feelings may be important feedback for the enterprise organization as it may permit the enterprise organization to better tailor their products/devices/treatments to their consumers. Accordingly, the UX computing system may distill observations into a base common quanta (e.g., aspects and/or moments) that may be important for comparisons across different contexts and studies. For example, one study may be for assessing user experiences during dialysis treatments in a patient's home and another study may be for overall user experiences for inpatient care. Traditionally, it may be difficult to assess similarities between these different studies. However, by being able to aggregate experiences across different studies together, the UX computing system may provide a more holistic and comprehensive model of actors across all of these studies. Furthermore, the UX computing system may be able to provide models (e.g., empathy gardens, actor models, and/or journey matrices) that are more fundamentally dynamic and adaptive to new findings including being able to continuously explore, innovate, and expand upon previous knowledge. Therefore, the UX computing system may assist in demystifying the user journey information and permit the enterprise organization to make more informed design decisions and create better user experiences in the future.

By first distilling the information into its basic elements and deriving comparisons based on standardized taxonomies, an advantage of using the UX computing system may include being able to compare data from multiple different studies to determine similarities, connections, and/or other relationships that might be missed otherwise. In addition, by using tools that focus solely on the study as an independent element, the UX computing system may be able to better view users as emergent patterns from across many different experiences and/or studies with them. Also, the UX computing system may be used to lose less information between studies, identify additional relationships/connections, provide a stronger return value for each study, create an opportunity for deeper research-based collaboration across various departments within an enterprise organization, and/or make connections within the data that allows for deeper and more informed questions in future studies. Further, the UX computing system may provide the benefit of having a centralized catalog of study data and also artifacts that provide the advantage of easier transfer of knowledge between employees as well as the ability to more easily find relevant information. Additionally, the UX computing system may permit the information to stay "alive." By staying "alive", the UX computing system's understanding of the users might not be siloed into a series of studies, but rather it may be a chain of information that permits the UX computing system to evolve its understanding without losing old findings or continually going over the same ground.

Examples of the present application utilize, collect, and process user experience data, including studies, surveys/survey data, observational tasks, user tasks, user feedback and/or other information, to determine actor models describing representative actors using products or services associated with the enterprise organization and/or journey matrices charting the exposure and interactions of these actor models over a period of time. For instance, in some examples, the UX computing system may receive multiple studies about user experiences with a product, machine, tool, service, and so on. The UX computing system may convert these studies, which may be in a non-standardized data format, into a standardized data format and then perform one or more algorithms (e.g., clustering and/or pattern discovery) to determine personas for an actor model and/or journey matrices for the actor model. The UX computing system may use a persona farm and/or a journey matrix generator to determine these personas and journey matrices. Additionally, and/or alternatively, the UX computing system may use the journey matrices to generate an empathy garden. This will be described in further detail below.

In a user experience context, a persona is a developed representation of actions and behavior of a hypothesized actor or group of actors. Personas may be synthesized from data collected about user experiences, including directly from users, and which include behavioral patterns, goals, skills, attitudes, with other details. Personas may provide common behaviors, outlooks, and potential desires and objections of actors matching a given persona.

A journey map may be a synthetic representation that describes how an actor interacts with a product or service over a period of time. In other words, a journey map may be a visualization of a single individual's relationship with a product/service/brand over a period of time and across different channels.

A persona farm may be a dynamic repository of user population facets and may store multiple personas. For example, there may be many personas for different types of patients as well as personas for a physician. The UX computing system may use the persona farm for aggregating, evolving, and generating data that may be used to generate, update, and store personas. By using persona farms, the UX computing system may automate many of the steps that are used to generate a persona and may transcend multiple, different studies based on received distilled information. A raw form of a persona within a Persona Farm may be referred to as an actor model. The actor model may be a description of a population (e.g., a group of actors) based on a defined context and research question. For example, a researcher may request information regarding how a clinician is during phases of a dialysis treatment for a patient. The UX computing system may use the persona farm to aggregate/analyze data from multiple different studies and use the result to determine a persona for this actor model. Additionally, and/or alternatively, the UX computing system may use the persona farm to update (e.g., add) existing actor models already within the persona farm with new findings (e.g., newly generated personas, newly received studies, and/or updated personas), which may add new depth and understanding to that representation of a particular population.

A journey matrix generator may be a feature that is used by the UX computing system to organize one or more moments from an actor model to generate a journey matrix. The journey matrix generator may further be used to determine average temporal representations of complex user experiences. For example, a journey map may tell a story of a single actor using a chain of sequential moments. However, a researcher may seek to understand a hypothetical journey or story of an actor model such as a clinician during a patient's dialysis treatment including the potential moments that may occur for the actor model. The UX computing system may use the journey matrix generator to generate a journey matrix (e.g., a hypothetical journey or story with a sequential chain of moments) for the requested actor model using the determined actor model from the persona farm and/or by analyzing the data from the studies. In other words, the UX computing system might not be able to generate journey maps for a sole actor from a study, but may also be able to generate a journey matrix for a requested actor model by determining intersecting journeys between multiple studies. This may be used for potential topics in new studies. For example, the UX computing system may determine a moment that matters in a journey matrix for an actor model such as patients undergoing dialysis treatment at home. After reviewing the moment that matters, a researcher may realize that another actor model is generally present during this moment (e.g., a physician or nephrologist). As such, by using the journey matrix generator, the UX computing system may generate and/or provide information that may be used to identify new opportunities such as an opportunity to investigate or perform a new study on a secondary population experience (e.g., the physician or nephrologist), which may improve the overall situation for both the original actor (e.g., patient) as well as for the secondary population experience. In other words, the UX computing system may be used to see across the journeys to create a more complete picture of what is happening in different situations.

An actor may be an emergent representation of an individual or user within a study. The actor may be a specific user that may be part of multiple studies that they may have participated within. In some instances, an actor may be a direct participant (e.g., patient) of the study. In other instances, an actor might not be a direct participant of the study, but someone else such as a nephrologist, physician, or caretaker that was mentioned/identified within a study.

FIG. 1 is a schematic illustration showing an example user experience environment 100 in a medical treatment context for which the system described herein may be utilized. In the environment 100, one or more users/patients 112a, 112b may engage and interact with one or more medical treatments stations 100a, 100b that may include machines, tubing, components, displays and interfaces. As a result of their experiences, the user(s) will have interactions and form conclusions about their user experience in connection with their engagement with and within the environment 100. Although two stations 100a, 100b are shown, those skilled in the art will appreciate that the system described herein may support more than or less than two stations, including a station at the home of a user. Furthermore, the stations 100a, 100b can be in locations remote from each other. For example, the stations 100a, 100b can be located in a clinical setting (e.g., a hospital or a dialysis clinic) or a non-clinical setting (e.g., at a home of a dialysis patient receiving hemodialysis or peritoneal dialysis using a home-based system). As further discussed in detail herein, the system described herein enables the gathering, consolidating and/or processing of user experience information in multiple contexts and environments, like the environment 100, from across the enterprise organization. It is noted that user experience information may be collected from the user 112a, 112b and/or from other types of users of the medical treatment stations 100a, 100b, including caregivers, technicians or clinicians and others.

The medical treatment stations 100a, 100b comprise an electronic data interface (e.g., a display screen, a computer-driver interface, or a touch screen) 102a, 102b that provides a visual and possibly tactile interface with a user and a digital processor 104 that controls the display screen 102*a*, 102*b* (e.g., vis-a-vis the display of prompts, as well as the input, display, communication, collection and/or storage of the information therefrom and thereto), and that interfaces with other such database systems 106, 108 (data storage mechanisms such as databases, servers, or otherwise), as well as with medical treatment apparatus, such as dialysis machines 110*a*, 110*b* (e.g. hemodialysis or peritoneal dialysis machines). The display screen 102*a*, 102*b* interface and the method of condition-based information transfer can allow customized content to be automatically and/or manually chosen by a user 112*a*, 112*b* for delivery to the user 112*a*, 112*b* in real time based on a medical condition of the patient 112*a*, 112*b* at the machines 110*a*, 110*b*.

The condition-based information transfer includes one or both of receiving medical condition information from the patient treatment station 100*a*, 100*b* and delivering content from the databases 106, 108 to the patients 112*a*, 112*b* (via the screens 102*a*, 102*b*) based on the received medical condition information. The customized information delivered to the display screens 102*a*, 102*b* can include textual, audio, video, and/or other education material that includes clinical data, which can facilitate the improvement of clinical outcome through education and patient participation in their own care, and entertainment, which can improve overall patient satisfaction with their treatment, improve patient compliance with prescribed treatment times, and provide a relaxing atmosphere that can positively affect overall clinical outcomes. The customized information received from the patients 112*a*, 112*b* can include medical data automatically gathered from the machines 110*a*, 110*b* and/or from other devices coupled to the patients 112*a*, 112*b*. The patients 112*a*, 112*b* can also transfer information to the processor 104 in response to content on the display screens 102*a*, 102*b*, such as choices of additional content for delivery or answers to survey questions.

As shown, the stations 100*a*, 100*b* are each associated with a medical treatment apparatus 110*a*, 110*b* (in this embodiment, hemodialysis machines) of the type commonly known in the art. The display screens 102*a*, 102*b* of the stations 100*a*, 100*b* are in electronic communication with the processor 104 (or otherwise coupled thereto) for use by a user such as a patient 112*a*, 112*b* being treated with the dialysis machines 110*a*, 110*b*, a nurse, a patient care technician, or other health care provider. Although two stations 100*a*, 100*b* are shown, those skilled in the art will appreciate that the processor 104 and the storage mechanisms 106, 108 may support more than or less than two stations. Furthermore, the stations 100*a*, 100*b* can be in locations remote from each other and/or the processor 104.

The stations 100*a*, 100*b* can each include a touch screen display 102*a*, 102*b*, the digital data processor 104, and a gateway 114. The touch screen displays 102*a*, 102*b* can each include a conventional device of that type known in the art for visual and/or tactile interface with an operator—here, patients 112*a*, 112*b*—operated in accord with the teachings hereof. The units 102*a*, 102*b* can be based on liquid crystal display technology, cathode ray display technology, or otherwise. The displays 102*a*, 102*b* are sized and provides resolution sufficient to display and collect information of the type described or are otherwise suitable for the digital data environment for which it is used. The displays 102*a*, 102*b* may be adapted for ready cleaning and/or sanitization, particularly when used in a clinical environment where multiple people typically use the displays 102*a*, 102*b*.

Additionally, while the displays 102*a*, 102*b* may include touch screens, the display devices 102*a*, 102*b* can include any device capable of displaying information to a user, e.g., a personal computer, a television, a portable digital device, or any other electronic display device. Furthermore, the displays 102*a*, 102*b* can have any configuration where they may be made easily, comfortably accessible to the patient 112*a*, 112*b*, such as on a rolling stand 116 (left display 102*a*), on an adjustable arm 118 (right display 102*b*), or otherwise. In other embodiments, the displays 102*a*, 102*b* may be more fully portable (e.g., lightweight and with carrying handles), fixed (e.g., wall-mounted or cabinet-mounted) or otherwise.

The displays 102*a*, 102*b* may be adapted to provide an ergonomic work station such that data entry puts a minimal stress on the patients 112*a*, 112*b*. The height and angle of the displays 102*a*, 102*b* can facilitate data entry and minimize the risk of repetitive stress disorders. The digital data processor 104 can include an embedded processor, personal computer, workstation, minicomputer, mainframe or other digital data processing device, as adapted in accord with the teachings hereof. The digital data processor 104 may be a standalone device or may be integral to one or more other components of the illustrated system, e.g., the touch screens 102*a*, 102*b* and/or medical treatment apparatus 110*a*, 110*b*. It may, moreover, be coupled for communication over communication links 120 with the touch screen displays 102*a*, 102*b* and the gateway 114 via any combination of wireless connection (e.g., BLUETOOTH, WIFI, or otherwise), wired connection (e.g. Ethernet), or otherwise.

Communication on one or more of the communication links 120 (which may include more or fewer linked connections than those shown in FIG. 1) may be secured with an appropriate security or encryption protocol or mechanism. The communication links 120 may be wired communication links and/or wireless communication links using wireless connections facilitated via short range or local area networks, such as BLUETOOTH or WIFI networks. The processor 104 can also be in communication with a data entry device such as a touch screen 122 that provides a visual and tactile interface with an administrator, e.g., a nurse, patient care technician, or other medical personnel. Through the touch screen 122, a user can coordinate input, display, communication, collection, and/or storage of data between the displays 102*a*, 102*b*, the processor 104, and/or the storage mechanisms 106, 108. Although only one touch screen 122 is shown in this embodiment, there may be any number of such data entry devices.

The database systems 106, 108 may each include a database, a data queue, a buffer, a local or remote memory device, random access memory (RAM), a cache, a server, or digital data storage device of the type known in the art, as adapted in accord with the teachings hereof. The databases 106, 108 are adapted to communicate with the displays 102*a*, 102*b* (via the processor 104) over one or more communication links 120 and possibly over a network 124, as described herein. Although the storage mechanisms 106, 108 are shown as separate elements from the processor 104 in this illustrated embodiment, the storage mechanisms 106, 108 can be integral to the processor 104, or the storage mechanisms 106, 108 can otherwise be combined into one storage mechanism or separated into one or more other storage mechanisms. Furthermore, the databases 106, 108 may communicate using the same or different network 124, which can itself include one or more interconnected networks. One or both of the storage mechanisms 106, 108 may be secured using a variety of appropriate encryption techniques.

In the illustrated embodiment, operation of the stations 100a, 100b in general, and of the touch screens 102a, 102b in particular, are controlled by the processor 104. To this end, and to the extent that this description attributes control and data processor functionality to the touch screens 102a, 102b, it will be appreciated that such control and data processing is provided by the processor 104. Similarly, control and data processing of the storage mechanisms 106, 108 is provided by the processor 104.

The gateway 114 provides communication coupling between the digital data processor 104 (and the storage mechanisms 106, 108) and the medical treatment apparatus (here, dialysis machines) 110a, 110b. In the illustrated embodiment, the gateway 114 may be a Universal Serial Bus (USB) hub. In other embodiments, the gateway 114 can take on other form factors (electrical and/or physical), such as Ethernet, serial cabling, and so forth, suitable for transmitting data to/from the processor 104 and the apparatus 110a, 110b and/or the display 102a, 102b. Moreover, the illustrated gateway 114 may include wireless communication capabilities (e.g., based on BLUETOOTH, WIFI, etc.), consistent with the aforesaid purpose. Regardless, the gateway 114 transmits data in a common protocol defined between the processor 104 and the treatment apparatus 110a, 110b. In the illustrated embodiment, the gateway 114 is a standalone device that is coupled with the processor 104 and the apparatus 110a, 110b via cabling, as shown, though in other embodiments it may be a standalone wireless gateway and/or may be integral with one of more of the other system components (e.g., the processor 104, the storage mechanisms 106, 108, and/or the apparatus 110a, 110b).

Figure 2:
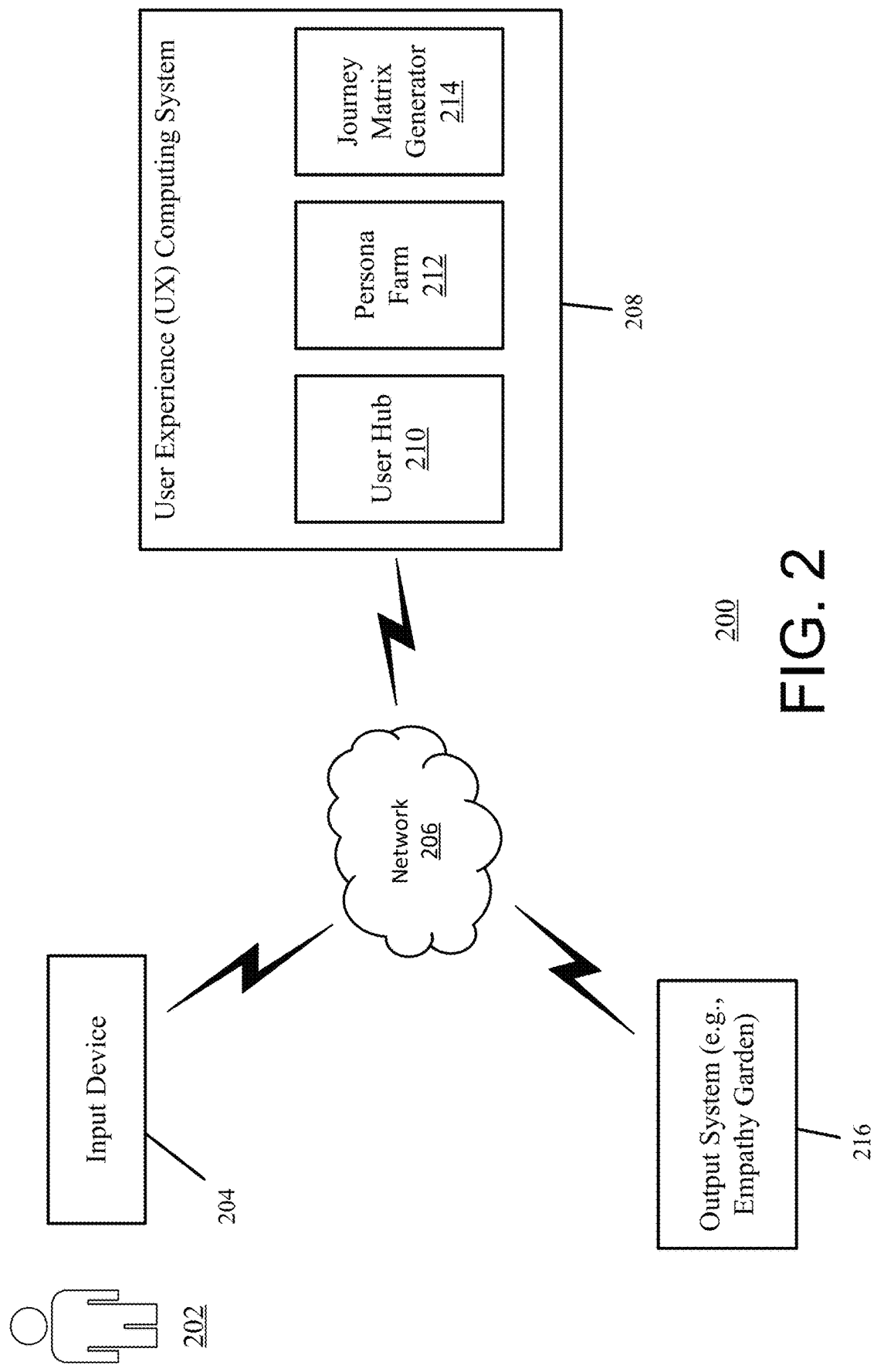
FIG. 2 is a simplified block diagram depicting an exemplary computing environment in accordance with one or more examples of the present application.

FIG. 2 depicts an exemplary computing environment 200 in accordance with one or more examples of the present application. The computing environment 200 includes an input device 204, an output system 216, a network 206, and a UX computing system 208. An operator 202 may be associated with the input device 204 and may enter information about their user experiences as a result of their interactions with the devices and components of one or more of the medical treatment stations 100a, 100b.

The entities within the environment 200 such as the input device 204, the UX computing system 208, and/or the output system 216 may be in communication with other systems within the environment 200 via the network 206. The network 206 may be a global area network (GAN) such as the Internet, a wide area network (WAN), a local area network (LAN), or any other type of network or combination of networks. The network 206 may provide a wireline, wireless, or a combination of wireline and wireless communication between the entities within the environment 100. Additionally, and/or alternatively, the input device 204 may be in communication with the UX computing system 208 without using the network 206.

The input device 204 may provide information to the UX computing system 208. The provided information may include, but is not limited to, surveys, studies, observational tasks, user tasks, and/or additional information related to user experiences with a product, tool, machine, and/or other items associated with the enterprise organization. For example, the input device 204 may display a screen that requests a user identification (ID) and a password. Based on authentication the user ID and password, a user may provide information such as one or more studies to the UX computing system 208.

In some examples, the input device 204 may include a user device that receives user input comprising one or more observational studies, interviews, surveys, and the like. The user device may provide the user input to the UX computing system 208. In such examples, the UX computing system 208 might not impact the way a study is being executed and/or how the information is captured by the investigation. Rather, after the study has been concluded and/or data from the study has been collected, the UX computing system 208 may be a repository for storing and processing this data.

Additionally, and/or alternatively, the input device 204 may include one or more existing repositories that stores one or more observational studies, interviews, surveys, and the like. For example, the repositories may store patient clinical data, demographic data, and/or existing survey tools. The repositories may export this information to the UX computing system 208. The UX computing system 208 may receive and store this data (when appropriate) into its database, which may allow for larger data sets in existing systems to be utilized without keying in more data or creating a secondary source of truth.

The input device 204 may be and/or include, but is not limited to, a desktop, repository, server, laptop, tablet, mobile device (e.g., smartphone device, or other mobile device), or any other type of computing device that generally comprises one or more communication components, one or more processing components, and one or more memory components. The input device 204 may be able to execute software applications managed by, in communication with, and/or otherwise associated with the enterprise organization. In various embodiments, the input device 204 may be implemented as or in connection with one or more of the digital data entry devices and systems shown and described in connection with FIG. 1.

The UX computing system 208 may be associated with an enterprise organization and may include one or more computing devices, computing platforms, systems, servers, and/or other apparatuses capable of performing tasks, functions, and/or other actions for the enterprise organization. For example, the UX computing system 208 may use the information (e.g., studies) from the input device 204 to determine one or more personas and/or one or more journey maps.

In some examples, the UX computing system 208 may be implemented using one or more computing platforms, devices, servers, and/or apparatuses. In some variations, the UX computing system 208 may be implemented as engines, software functions, and/or applications. In other words, the functionalities of the UX computing system 208 and/or the UX computing system 208 may be implemented as software instructions stored in storage (e.g., memory) and executed by one or more processors. In some variations, the UX computing system 208 may be used for, focused on, and/or is associated with user experiences, customer experiences, human factors data, and/or other types of experiences.

The UX computing system 208 includes a user hub 210, a persona farm 212, and a journey matrix generator 214. The user hub 210 is a repository of user data that is stored at the "moment" level. In some instances, the user hub 210 may also determine (e.g., find) and/or share data, protocols, and other research assets. For example, by using the user hub 210, a researcher or operator may be able to identify research assets such as protocols and/or consent forms. For instance, the researcher or operator may be able to use the user hub 210 to open a study of interest and retrieve any documentation that may be stored within the user hub 210.

Furthermore, the user hub 210 may build and manage taxonomies and/or store information using a user hub information architecture. For example, the UX computing system 208 may continuously break down data into smaller and smaller data elements and may store each data elements with a classification identifier describing each stage of the data break down. For example, initially, the UX computing system 208 may receive multiple different studies. A study may be the largest data element to be stored within the user hub 210. Then, the UX computing system 208 may break down each study into protocols, which may be a definition of a section within a particular branch of a study and may include forms for collecting data in the study. The UX computing system 208 may further break down the protocols into sections with each section being either structured (e.g., where a researcher may know the stories/questions to be answered ahead of collecting the data) or unstructured (e.g., where the study is more open ended and does not have pre-defined stories). Afterwards, the UX computing system 208 may break down each section into stories, may break down the stories into moments, and may further break down the moments into aspects. Stories are topic clusters that exist within the section. Each story may have multiple moments, which are packages of variables used for gathering different types of information within a study and at a time period within the study. In some instances, each section of a study may have only one moment type. Moments may further be decomposed into aspects. An aspect of a moment may be one specific type of information (e.g., feelings, people, places, and so on) and is of a single data form (e.g., nominal, ordinal, prose, and so on). After breaking down the studies using the user hub information architecture, the UX computing system 208 may store the particular data element with a classification identifier associated with the architecture (e.g., whether the data element is a study, protocol, section, story, moment, and/or aspect). Subsequently, the UX computing system 208 may use these data elements and/or classification identifiers as a template for future studies, which may save time and improve consistency across studies. Furthermore, the data elements may be standardized and defined by shared taxonomies, which may be critical for cross-study comparisons.

In some instances, in structured sections, the stories and moments may be able to be easily identified/classified beforehand. For instance, in structured sections/studies, the story may be a question asked to a participant about a particular experience and a moment may be the answer from the participant.

In other instances, in unstructured sections or studies, the stories and moments might not be able to be identified/classified beforehand. For example, an unstructured section may include unstructured interviews, which may include a user discussing various aspects of their experiences. As such, the interview may be a stream of consciousness from a user, which might be difficult to classify beforehand. In such instances, operator input may be used to identify the stories and moments from the unstructured interviews. For example, a researcher or operator may listen to or read a transcript of an unstructured interview and provide operator input as to parts of the interview that are stories and parts of the interview that are moments. The user hub 210 may receive the operator input and accordingly use the operator input to classify different sections of the interview as stories, moments, and/or aspects. In other words, the user hub 210 may provide tools to an operator/researcher for manually clustering (e.g., using a card-sort-like mechanism) and classifying moments into stories such that it may be used by the persona farm 212 and/or journey matrix generator 214.

In some examples, the user hub 210 may automate the break-down of the data elements and/or automate classifications using machine learning algorithms such as natural language processing (NLP) artificial intelligence (AI) algorithms. For example, for unstructured sections such as unstructured interviews, the user hub 210 may use NLP AI algorithms to determine the stories, moments, and/or aspects from the unstructured sections.

In other words, the UX computing system 208 may receive multiple different studies that may be in different data formats (e.g., may include unstructured and/or structured sections/studies). As such, it might be difficult to identify useful information from these studies. Accordingly, the UX computing system 208 may standardize the studies such that the data from the studies may be broken down into common, standardized data elements with their respective identifiers (e.g., studies, protocols, sections, stories, moments, and/or aspects). For example, the UX computing system 208 may use operator input and/or NLP AI algorithms to standardize the data elements. After breaking down and standardizing the data, the UX computing system 208 may compare and/or use this data to identify important aspects within the data and/or to create personas, actor models, journey matrices, and empathy gardens. This will be described below.

The persona farm 212 is a living repository of actor models, which are used to create personas. The actor models may be dynamically generated from asynchronous observational user data across multiple sources. In other words, the persona farm 212 may generate actor models, which may be a representation of a population. An actor may be the raw data that is received by the persona farm 212 and from the user hub 210. A researcher may seek to understand more information about a particular actor model such as about a nephrologist. The persona farm 212 may analyze data from the user hub 210 including analyzing multiple different studies to determine the stories, moments, and/or aspects (e.g., feelings) that appear for the nephrologists. Based on the analysis, the persona farm 212 may generate actor models for nephrologists. The actor model may include the stories, moments, and aspects such as feelings of the nephrologists when interacting with patients and/or particular products/devices at particular instances in time.

The journey matrix generator 214 is a tool for dynamically generating journey maps and/or matrices and exploring how different journeys may interact. For example, a journey map may be an answer to a specific research question and be associated with one particular user or person. The journey map may tell a story of this specific person (e.g., how a patient was undergoing dialysis treatment). The journey matrix generator 214 may further generate a journey matrix for an actor model such as moments a nephrologist may encounter during a dialysis treatment for a patient. The journey matrix for the actor model may include moments from various different actors that are put into a temporal order. For example, the studies may indicate how multiple different patients were like during dialysis treatment. The studies may include moments such as one or more patients were frustrated when an alarm occurred at certain times during their dialysis treatment. Using this information, the journey matrix generator 214 may generate a journey matrix for nephrologists of moments that a nephrologist may encounter when a patient undergoes dialysis treatment. For example, one moment within the journey matrix may be how a nephrologist would react to the patients being frustrated by the alarm. To put it another way, a journey matrix may be associated with a particular actor model (e.g., nephrologists)

whereas a journey map may be associated with a particular individual that was observed during one or more studies. As such, the journey map may be associated with one or two studies. However, a journey matrix is not limited to single threaded journeys and may be associated with a general representation of a population of users.

By automating the generation of the personas and journey matrices, this may prevent fewer assumptions that may skew or impact the data in any way. For example, if a researcher attempts to generate personas/journey matrices by hand, the researcher may introduce their own biases into this generation such as having a pre-conceived notion that a nephrologist may interact in a certain manner using the researcher's own past experiences. However, by using the persona farm 212 and the journey matrix generator 214 to generate personas and journey matrices for actor models, less researcher bias may be introduced into the generated personas/journey matrices.

The user hub 210, the persona farm 212, and the journey matrix generator 214 will be described in further detail below.

The output system 216 may be a component, device, or other information distribution system used in the display, presentation and/or distribution of the information and results gathered and processed using the UX computing system 208. The output system 216 may facilitate the creation of an immersive experience for communicating data about the user experiences of patients and other users of products and services, such as dialysis machines and dialysis services, to the audiences (e.g. developers, engineers, designers and other creators) engaged in the development of the product(s) and provided services at the enterprise organization. For example, as further described in detail elsewhere herein, in an embodiment, the output system 216 may be implemented as an "empathy garden" for the purposes of presenting the information and results from the UX computing system 208 in a way to foster a culture of cultivating empathy throughout the enterprise organization and beyond in connection with product development and service delivery.

It will be appreciated that the computing environment 200 depicted in FIG. 2 is merely exemplary. The principles discussed herein are also applicable to other types of environments, configurations, entities, and equipment.

Figure 3:
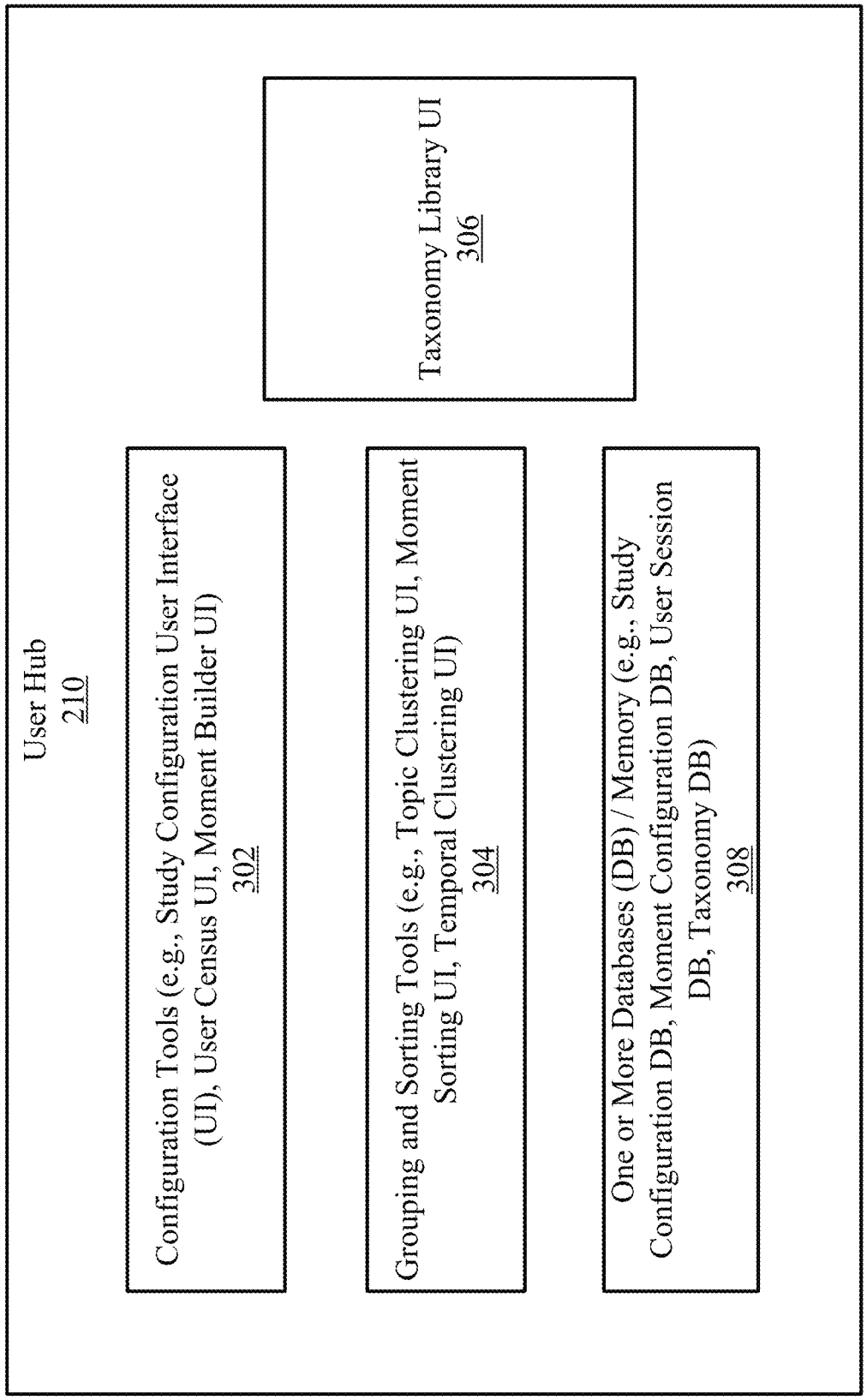
FIG. 3 is a simplified block diagram of the user hub of the exemplary computing environment of FIG. 2.

FIG. 3 depicts an exemplary user hub 210 of the computing environment 200 in accordance with one or more examples of the present application. For example, the user hub 210 includes configuration tools 302, group and sorting tools 304, a taxonomy library user interface (UI) 306, and one or more databases (DB)/memory 308. The configuration tools 302 and/or the group and sorting tools 304 may include one or more UIs that may be used by a researcher to analyze, process, and/or categorize the data. For example, the UIs may be used break down the data into smaller chunks and/or classify the data using the user hub information architecture. Additionally, and/or alternatively, the user hub 210 may automate this break down/classification process such as by using an NLP AI algorithm. The configuration tools 302 includes a study configuration UI, a user census UI, and/or a moment builder UI. The grouping and sorting tools 304 includes a topic clustering UI, a moment sorting UI, and a temporal clustering UI. The taxonomy library UI 306 is used in creating information units that may be compared and integrated. This represents communal semantics that bridges data from different studies.

The DBs/memory 308 includes a study configuration DB, a moment configuration DB, a user session DB, and a taxonomy DB. The study configuration DB is used to store study details. The user session DB is the main storage mechanism for data across the received studies and may store the data that was collected from the study (e.g., normative sections or other aspects of a study). For example, the study configuration DB may be the questions from the studies and the user session DB may be the answers to the questions from the study. In some instances, the patterns (e.g., the configuration of a study, section, or moment type within the user hub 210) may be cloned or duplicated within the system, creating consistency between protocols and reducing overall configuration time. The moment configuration DB includes moments, which are the basic building blocks for data representation. Similar to studies, moments may be built custom or cloned/duplicated from existing moment definitions. The taxonomy DB is a database that stores the taxonomy data. For example, the taxonomy DB may include associated tables and items that may be entered within the system. The taxonomy DB may be libraries of common language terms and store the common language that is used across all of the studies. For example, for gender, the common language terms may include male, female, non-binary, and so on. For feelings, the common language terms may include separate categories of feelings and specific terms for each category (e.g., the category may be emotional feelings and the specific terms may include happy, hurt, emotional, and so on). The taxonomy DB may further be associated with different products, devices, and/or treatments. Additionally, and/or alternatively, the taxonomy DB may be for different actors such as nurses, nephrologists, and so on.

Figure 4:
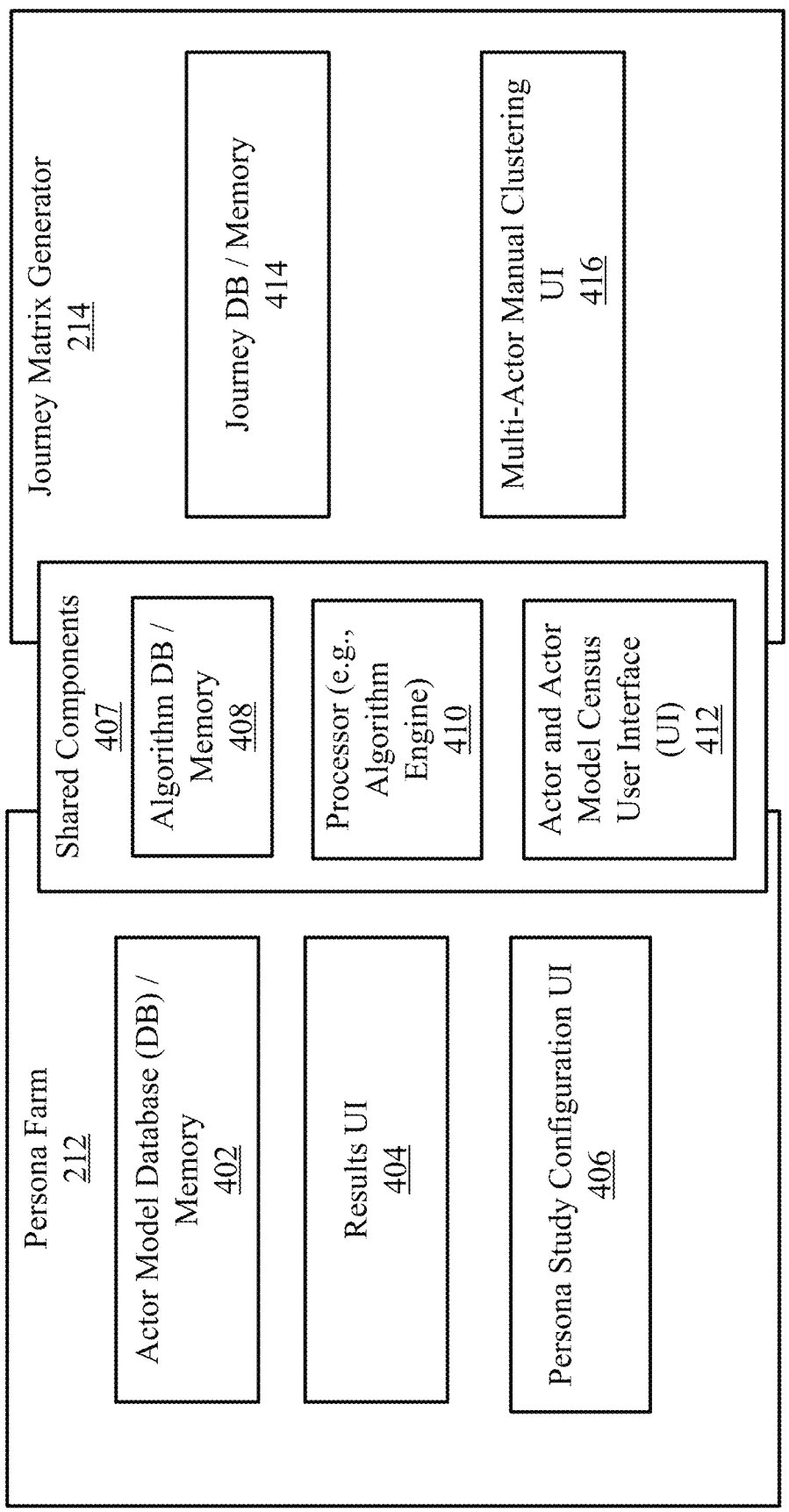
FIG. 4 is a simplified block diagram of the persona farm and journey matrix of the exemplary computing environment of FIG. 2.

FIG. 4 depicts an exemplary persona farm 212 and journey matrix generator 214 of the computing environment 200 in accordance with one or more examples of the present application. In particular, the figure shows the persona farm 212, the journey matrix generator 214, and shared components 407. The shared components 407 may be components or entities within the persona farm 212 and/or the journey matrix generator 214. Additionally, and/or alternatively, the shared components 407 may include components or entities that are separate from both the persona farm 212 and the journey matrix generator 214.

In operation, the actor and actor model census user interface (UI) 412 may receive information from the user hub 210. This information may include data such as actor experiences with a particular product, tool, and/or machine associated with the enterprise organization. In some instances, the information may include broken down data elements and their associated user hub information architecture classification identifiers (e.g., study, protocol, section, story, moment, and/or aspect). The actor and actor model census UI 412 provides information to the persona study configuration UI 406, the processor (e.g., algorithm engine) 410, and/or the multi-user manual clustering UI 416. The algorithm engine 410 uses one or more algorithms (e.g., automated clustering and/or pattern discovery algorithms) to determine clusters and/or patterns associated with the information. The algorithm engine 410 provides the results to the algorithm DB/memory 408. The algorithm DB/memory 408 stores the results.

The persona study configuration UI 406 receives information from the actor and actor model census UI 412 and/or retrieves information from the algorithm DB 408. The persona study configuration UI 406 enables an operator (e.g., researcher) to configure the aspects of actor measurements that are included in determining the personas and how these actor measurements are considered in the modeling process. For example, the researcher may use the persona study configuration UI 406 to request the persona farm 212 to generate a persona for a particular actor model. The results UI 404 provides results (e.g., determined personas) back to the researcher for evaluation and/or configuration into a persona template for presentations. The results UI 404 may use the configurations input using the persona study configuration UI 406 to determine and provide the results. The actor model DB/memory 402 is a database that stores generated persona models for actor models, which can later be turned into consumable personas for presentation.

The multi-actor manual clustering UI 416 receives information from the actor and actor model census UI 412 and may further retrieve information from the algorithm DB 408 and/or the actor model DB 402. The multi-user manual clustering UI 416 allows for manual corrections and clustering after the algorithm has completed. In other words, it may be used by researchers to organize the moments from multiple actors into a journey matrix for the actor model. The multi-user manual clustering UI 416 provides information to the journey DB/memory 414. The journey DB/memory 414 stores the generated journey matrices.

Figure 5:
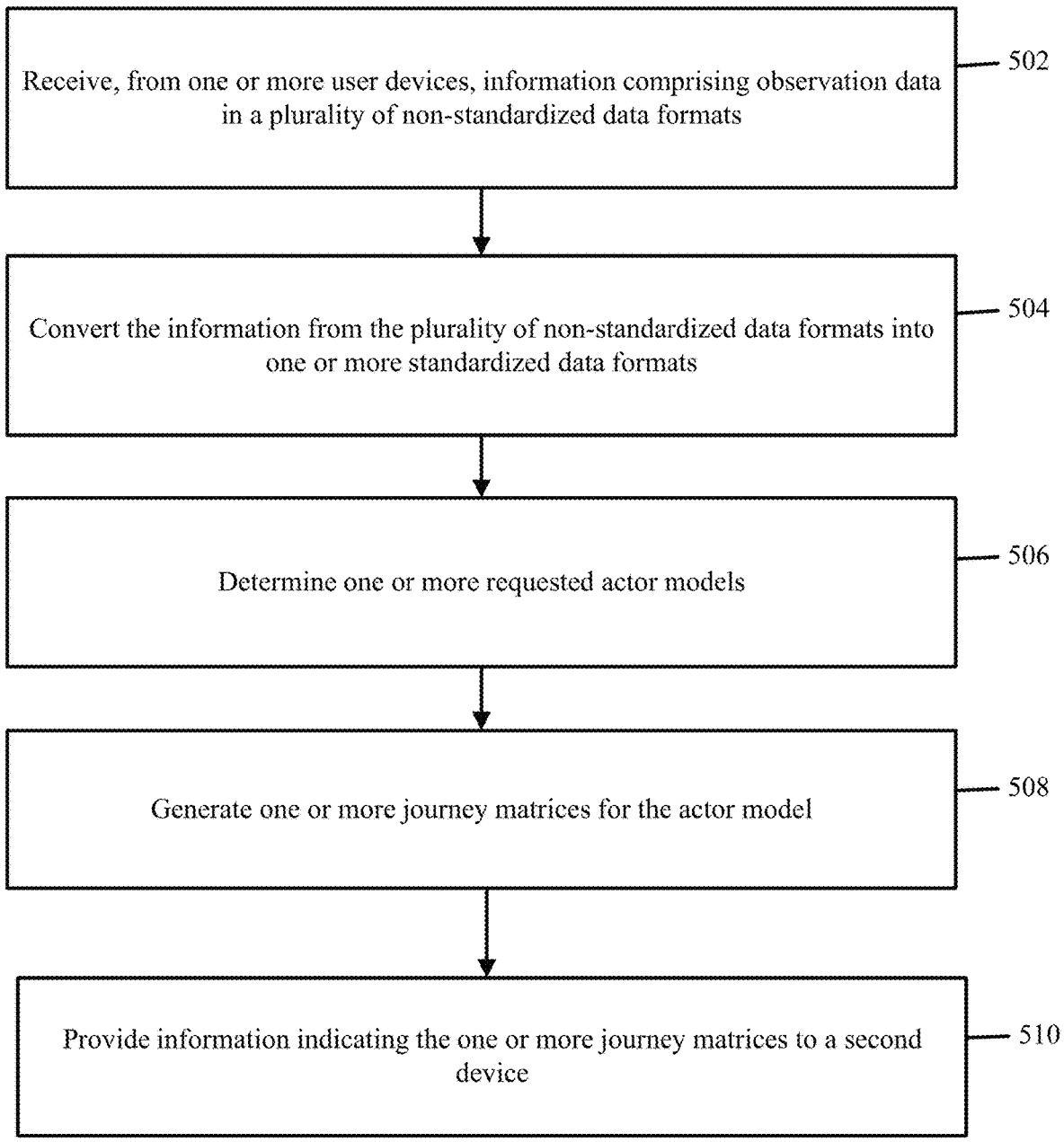
FIG. 5 is a flowchart of an exemplary process for determining a persona and generating a journey map in accordance with one or more examples of the present application.

FIG. 5 is a flowchart of an exemplary process for determining personas and/or journey maps for an individual or a group of individuals in accordance with one or more examples of the present application. In operation, at block 502, the UX computing system 208 receives information including observation data in non-standardized data formats. For example, as described above, the UX computing system 208 may receive multiple studies from a data repository and/or manually entered in by a researcher using a user device. The studies may include the interview data as a series of clustered moments associated with an actor. In some instances, the observation data may further include surveys/survey data, observational tasks, user tasks, user feedback and/or other information.

At block 504, the UX computing system 208 converts the information from the plurality of non-standardized data formats into one or more standardized data formats. For example, the studies may include non-standardized data formats such as structured and unstructured sections/studies. The UX computing system 208 may convert these non-standardized data formats into standardized data formats such as by breaking down the studies into smaller chunks of data (e.g., smaller data elements) and classifying each of the chunks of data using the user hub information architecture classification identifiers (e.g., study, protocol, section, story, moment, and/or aspect), which is described above. In some instances, the UX computing system 208 may use operator input and/or NLP AI algorithms to convert the observation data into standardized data formats.

At block 506, the UX computing system 208 determines one or more requested actor models. For example, the researcher may seek to understand more information about a particular actor model such as for a nephrologist. The UX computing system 208 may analyze the converted standardized data and generate an actor model for the particular actor model. The actor model may include stories, moments, and/or aspects from the received observation data at block 502.

At block 508, the UX computing system 208 generates one or more journey matrices for the actor model. The journey matrices may include sequential moments of a hypothetical experience that the actor model (e.g., nephrologist) may experience. For example, the journey matrix may include a plurality of sequential moments for a nephrologist throughout a dialysis treatment of a patient. Blocks 506 and 508 will be described in further detail in FIG. 6.

At block 510, the UX computing system 208 provides information indicating the one or more journey matrices to a second device such as the output system 216. The output system 216 may display the journey matrices. In some instances, the information may be used to generate an empathy garden. For example, an empathy garden may include the journey matrices and may further include additional information such as recordings from one or more actors, images collected from the studies, printed quotes taken directly from the actors, and/or simulation of activities that may install a sense of empathy and understanding for consumers of the empathy garden. In other words, the empathy garden may tell a story of a population-of-interest's (e.g., requested actor model) in a given context (e.g., during a dialysis treatment). For example, it may describe the journey a home patient experiences throughout their dialysis treatment.

Figure 6:
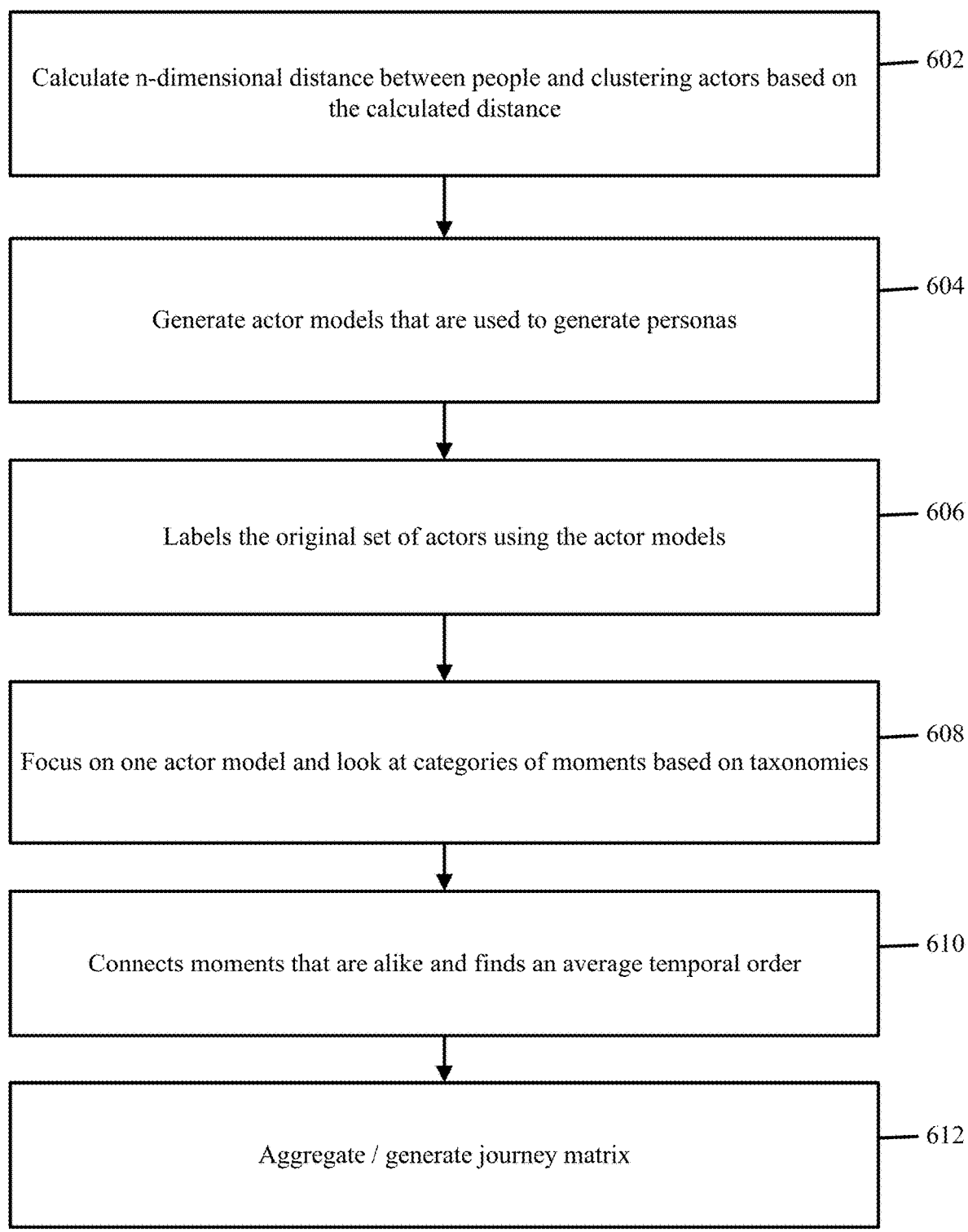
FIG. 6 is a flowchart of an exemplary process for determining a persona farm and generating a journey matrix in accordance with one or more examples of the present application.

FIG. 6 is another flowchart of another exemplary process for determining personas and/or journey maps in accordance with one or more examples of the present application. In particular, FIG. 6 describes an exemplary process 600 of the UX computing system 208 performing blocks 506 and 508.

Figure 7A:
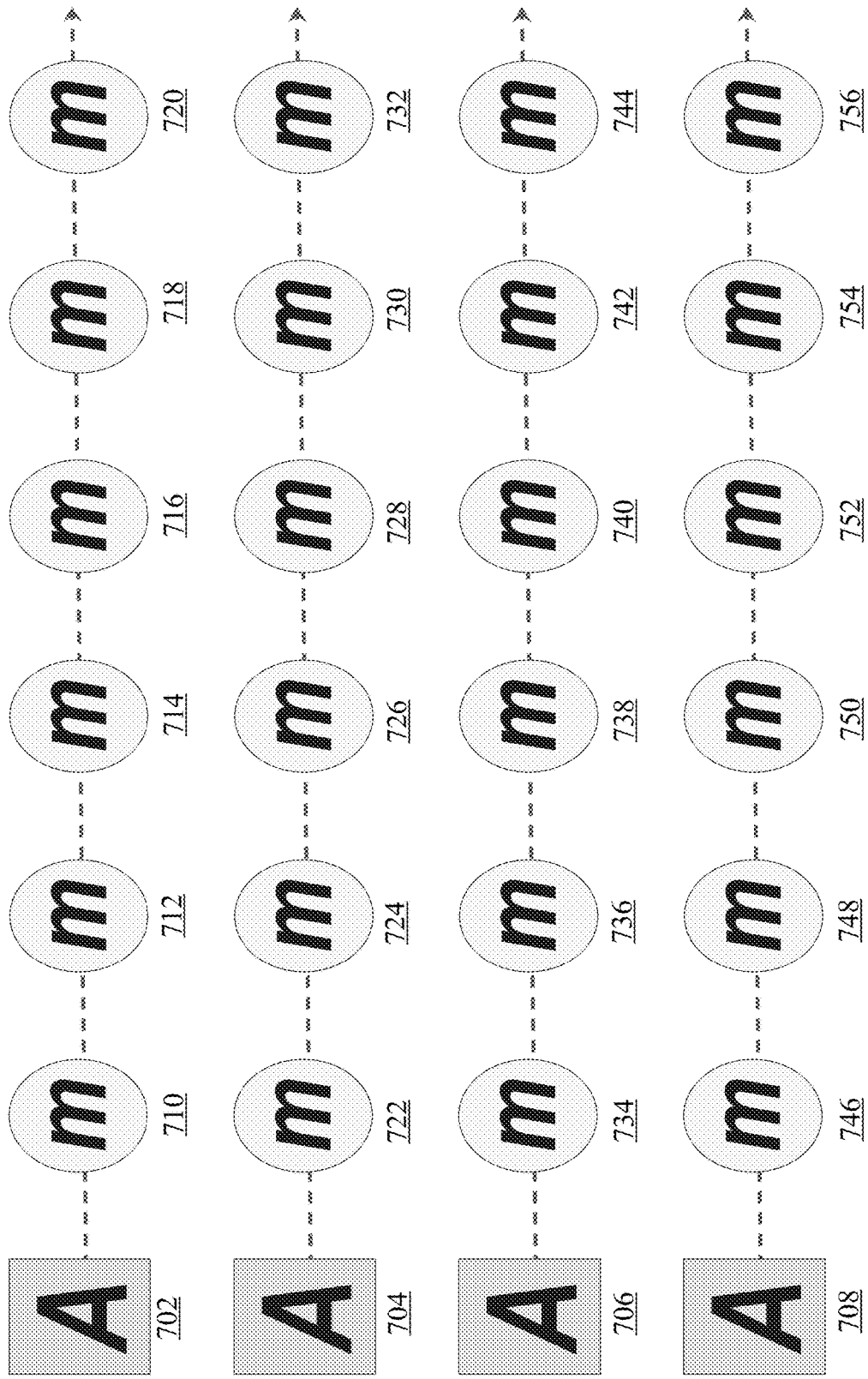
FIGS. 7*a* and 7*b* are exemplary graphical representations of the conversion of data into actor models and journey matrices in accordance with one or more examples of the present application.
Figure 7B:
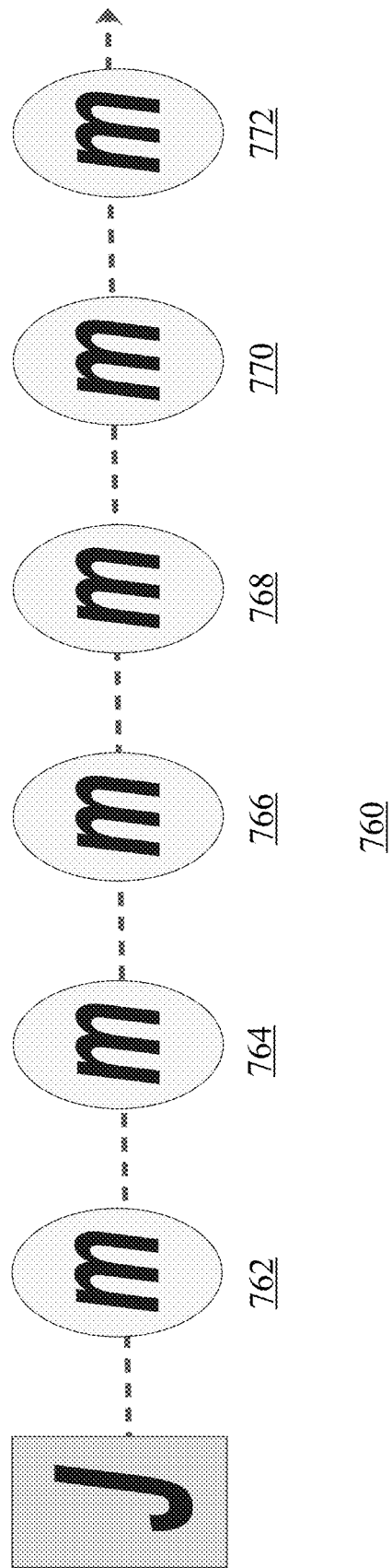

FIGS. 7a-7b are exemplary graphical representations of the conversion of data into actor models and journey matrices in accordance with one or more examples of the present application. FIGS. 7a-7b will be used to describe FIG. 6 in more detail.

In operation and as described above in block 502, the UX computing system 208 receives observation data as a series of clustered moments for many actors. FIG. 7a shows an exemplary graphical representation of the observation data as a series of sequential moments. For example, each of the actors 702-708 may be associated with multiple different moments. In some instances, these actors 702-708 may be from the same study. In other instances, they may be from different studies. The sequential moments may be a story for the actor. For example, the actor 702 may be a patient undergoing dialysis treatment and each moment may include information for an instance in time as to how the actor 702 was feeling, additional people that were present such as a caretaker or nephrologist, location where the moment occurred, and so on. Actors 704 and 706 may be other patients undergoing dialysis treatment. Actor 708 may be a caretaker or family member of a patient undergoing dialysis treatment. This caretaker or family member may be associated with actors 702-706 or may be associated with another patient.

Referring to FIG. 6, at block 602, the UX computing system 208 calculates an n-dimensional distance between actors and clusters the actors based on the calculated distance. The UX computing system 208 may cluster the actors together in order to find patterns between the actors and create models of similar individuals. The data from within these clusters (e.g., the moments within the clusters) may be used to generate personas. The clustering may be performed using any type of clustering technique such as the adaptive resonance theory 2 (ART2) algorithm.

In some examples, referring to FIG. 7a, the UX computing system 208 may analyze each of the moments for the actors 702-708 to calculate an n-dimensional distance between these actors and then cluster the actors based on the calculated distance. For instance, the UX computing system 208 may calculate the n-dimensional distances based on the data from the moments such as actors with the same height, look, build, and/or similar location or place where the moment occurred. Additionally, and/or alternatively, the UX computing system 208 may calculate the n-dimensional distances based on the feelings that happened within the moments to determine the emotional fingerprint and overlap between the different actors. For example, using the taxonomy database from the user hub 210, the UX computing system 208 may determine values such as binary values for each of the feelings and may use these values to calculate the n-dimensional distances/cluster the actors. For instance, two exemplary feelings that may be within the moments for the actors 702-708 may be happy or sad. The UX computing system 208 may use the taxonomy database to determine that if an actor is happy, the binary value may be 01. If sad, the binary value may be 10. If the actor is both happy and sad, then it may be 11. Based on these binary values for the feelings, the UX computing system 208 may calculate an n-dimensional distance between the actors and use them to cluster the actors.

Each of the actors 702-708 may be associated with a plurality of moments that define a journey map for the actor. For instance, actor 702 may be associated with moments 710-720, which define a journey for the actor 702. Similarly, actor 704 may be associated with moments 722-732, actor 706 may be associated with moments 734-744, and actor 708 may be associated with moments 746-756.

Only four actors are shown in FIG. 7a and described here for sake of simplicity, but in other examples, the UX computing system 208 may analyze moments for numerous actors including hundreds, thousands, and/or even millions of actors from across numerous studies. Furthermore, the UX computing system 208 may cluster these actors based on a calculated n-dimensional distance.

At block 604, the UX computing system 208 generates actor models that are used for personas. Actor models may be the mid-point between the dimensions that are used to describe a cluster and may be used for generating personas. For example, after clustering the actors at block 602, the UX computing system 208 may classify each of the clusters as an actor model. In other words, the UX computing system 208 may use an algorithm and/or operator input to cluster the actors into actor models. For instance, based on a certain distance between several of the actors, the UX computing system 208 may determine the actors as a cluster and classify them as an actor model. Additionally, and/or alternatively, the UX computing system 208 may display a graphical representation showing the actors plotted out by distance. The UX computing system 208 may receive operator input (e.g., the operator providing a boundary region for each actor model) indicating the actors that are to be clustered together such that they represent an actor model.

In some examples, the UX computing system 208 may provide an identifier for an actor model. For example, as mentioned above, the actor model may be a description of a population (e.g., a group of actors) based on a defined context. In some instances, the UX computing system 208 may receive operator input indicating the identifier (e.g., nephrologist, clinician, caretaker, patient undergoing dialysis treatment, patient feeling happy, and so on) associated with the actor model.

In some variations, the UX computing system 208 may update an existing actor model within the persona farm 212. For example, based on clustering the actors, the UX computing system 208 may determine the actors belong to an already existing actor model within the persona farm 212. The new actors may include additional moments. As such, the UX computing system 208 may update the already existing actor model with the new actors including the new moments.

In some instances, the UX computing system 208 may generate personas for the actor models. For instance, after clustering the actors into actor models, the UX computing system 208 may use the moments and/or actors from the actor models to generate personas. Additionally, and/or alternatively, the UX computing system 208 may use one or more pre-existing actor models within the persona farm 212 to generate the personas.

At block 606, the UX computing system 208 labels the original set of actors using the actor models. For example, after generating the actor models, the UX computing system 208 may label the original set of actors using the actor models and/or the identifier for the actor model. For instance, referring to FIG. 7a, actors 702-706 may associated with a particular actor model such as patients undergoing dialysis treatment and actor 708 as a clinician assisting with the dialysis treatment. The UX computing system 208 may label the actors 702-706 using the identifier patients undergoing dialysis treatment and label the actor 708 as clinician assisting with the dialysis treatment.

At block 608, the UX computing system 208 focuses on one actor model and looks at categories of moments based on taxonomies. For example, the UX computing system 208 may receive operator input from a researcher or operator indicating a request for a particular actor model. The request may indicate to generate a journey matrix for the particular actor model. The UX computing system 208 may focus on the actor model indicated by the request from the researcher. For instance, the researcher may seek to discover or would like to study a particular population such as how to make a particular product or treatment better or how to improve a user's experience with the product or treatment.

In some instances, the UX computing system 208 may look at or classify categories of moments based on particular taxonomies for the requested actor model. For example, the researcher may seek to understand more information regarding patients undergoing dialysis treatment (e.g., the actor model associated with actors 702-706). The UX computing system 208 may first filter out the actors based on the requested actor model. In other words, the UX computing system 208 may filter out actor 708 such that only actors 702-706 are left. Then, the UX computing system 208 may classify categories of moments based on particular taxonomies for the actors 702-706. For example, the UX computing system 208 may determine moments with particular feelings such as happy and classify each of these moments together. Furthermore, since the UX computing system 208 may determine moments that the actor felt relieved and classify these moments together.

At block 610, the UX computing system 208 connects the moments that are alike and finds an average temporal order. For example, different people may experience similar moments at different times. Accordingly, the UX computing system 208 may connect and/or determine moments that are similar for multiple actors throughout their own stories. For instance, referring to FIG. 7a, actor 702 may have felt happy at moment 712 and actor 706 may have felt happy at moment 742. These two moments 712 and 742 may be at different times. At block 610, the UX computing system 208 may connect moments 712 and 742 based on the actors 702 and 706 within the actor model feeling happy. Then, the UX computing system 208 may determine an average temporal order for these similar moments (e.g., average time period during the dialysis treatment associated with the moments 702 and 706).

In another example, as mentioned above, the story for an actor may indicate a particular event that occurred with its own associated feelings, other people present, product/treatment that was involved, and so on. The event may be followed by a separate event afterwards. For instance, at moment 724, the dialysis machine was giving actor 704 an alarm that they could not clear and actor 704 was frustrated and scared. This moment 724 may be followed by another moment 726 within the same story that described the next set of events within a chain such as the issue was resolved and the actor 704 felt a sense of relief and gratitude. Similarly, for actor 706, this may have occurred in moments 736 and 738. The UX computing system 208 may connect these chain of moments 724/726 with 736/738 and determine an average temporal order for these moments.

At block 612, the UX computing system 208 aggregates/generates a journey matrix for the actor model. For example, based on the request from the operator/researcher, the UX computing system 208 may aggregate and generate a journey matrix for the requested actor model based on determined similar moments and average temporal order from block 610. FIG. 7b shows an exemplary journey matrix 760 for a requested actor model 762. For instance, the journey matrix 760 shows a hypothetical story that may occur for the requested actor model of a patient undergoing dialysis treatment. The UX computing system 208 may use the moments from the actors 702-706 to generate the journey matrix 760. For example, as mentioned above, moment 764 from the journey matrix 760 may be associated with an actor being happy (e.g., actors 702 and 706 with moments 712 and 742). Based on the determined average temporal order and several of the actors from the actor model experiencing this moment, the UX computing system 208 may insert a moment into the hypothetical journey matrix of what a patient undergoing dialysis treatment may experience throughout their treatment. For instance, the UX computing system 208 may include moment 764 within the journey matrix as a moment that a potential population of dialysis patients experiences a happiness feeling. Furthermore, the UX computing system 208 may include moment 766 as a moment where the dialysis patients may experience an alarm on the dialysis machine, which leads to frustration and being scared (e.g., similar to moments 724 and 736). Additionally, the UX computing system 208 may include moment 768 as a moment where the issue was resolved and the dialysis patients may experience relief and gratitude.

In some examples, the UX computing system 208 aggregates/generates a journey matrix for the actor model based on operator input. For example, a researcher may review the similar moments from actors within the actor models and determine important moments (e.g., moments that matter). Based on the review, the researcher may provide operator input indicating for certain moments (e.g., the dialysis patients may experience happiness at some instance in time) to be incorporated within the journey matrix. In other examples, the UX computing system 208 may aggregate/generate the journey matrix automatically such as based on a threshold. For example, based on a certain percentage of actors within the actor model or based on a threshold value (e.g., 2 actors experiencing the moment), the UX computing system 208 may determine to incorporate one or more moments within the journey matrix.

In some variations, after generating the journey matrix, the UX computing system 208 may cause display of the journey matrix. For example, the UX computing system 208 may include one or more display devices that may display the journey matrix for the requested actor model to the researcher. Additionally, and/or alternatively, the UX computing system 208 may provide the generated journey matrix to a second device such as the output system 216. The second device (e.g., the system 216) may display the generated journey matrix.

Further to the system described herein, based on the user experience information and results derived from the UX computing system 208, an immersive presentation experience may be generated for communicating data about the experience of users to the internal enterprise organization audiences that are performing product and service development functions at the enterprise organization. One example implementation of a system for the presentation, display and/or distribution of the information and results from the UX computing system to the product development and service-providing audiences of the enterprise organization, may be referred to as an Empathy Garden. A function of the Empathy Garden is to foster a culture of cultivating empathy throughout the organization in connection with product and service development, particularly for employees whose job roles require few or no hands-on experiences with the user populations being served.

The Empathy Garden allows audience participants to experience a multi-sensory dive into the stories, experiences and/or other interactions of the users (patients, caregivers, technicians, clinicians etc.) generated from the processed user experience information of those users, gathered and processed via the UX computing system 208, who interacted with the medical treatment environment. The Empathy Garden may include, but is not limited to, digital and/or other types of displays, presentations and systems, that may include first-hand audio recordings, context specific imagery, and activities designed to allow participants to understand user data from the UX computing system 208 in a deeper and more meaningful way.

Figure 8:
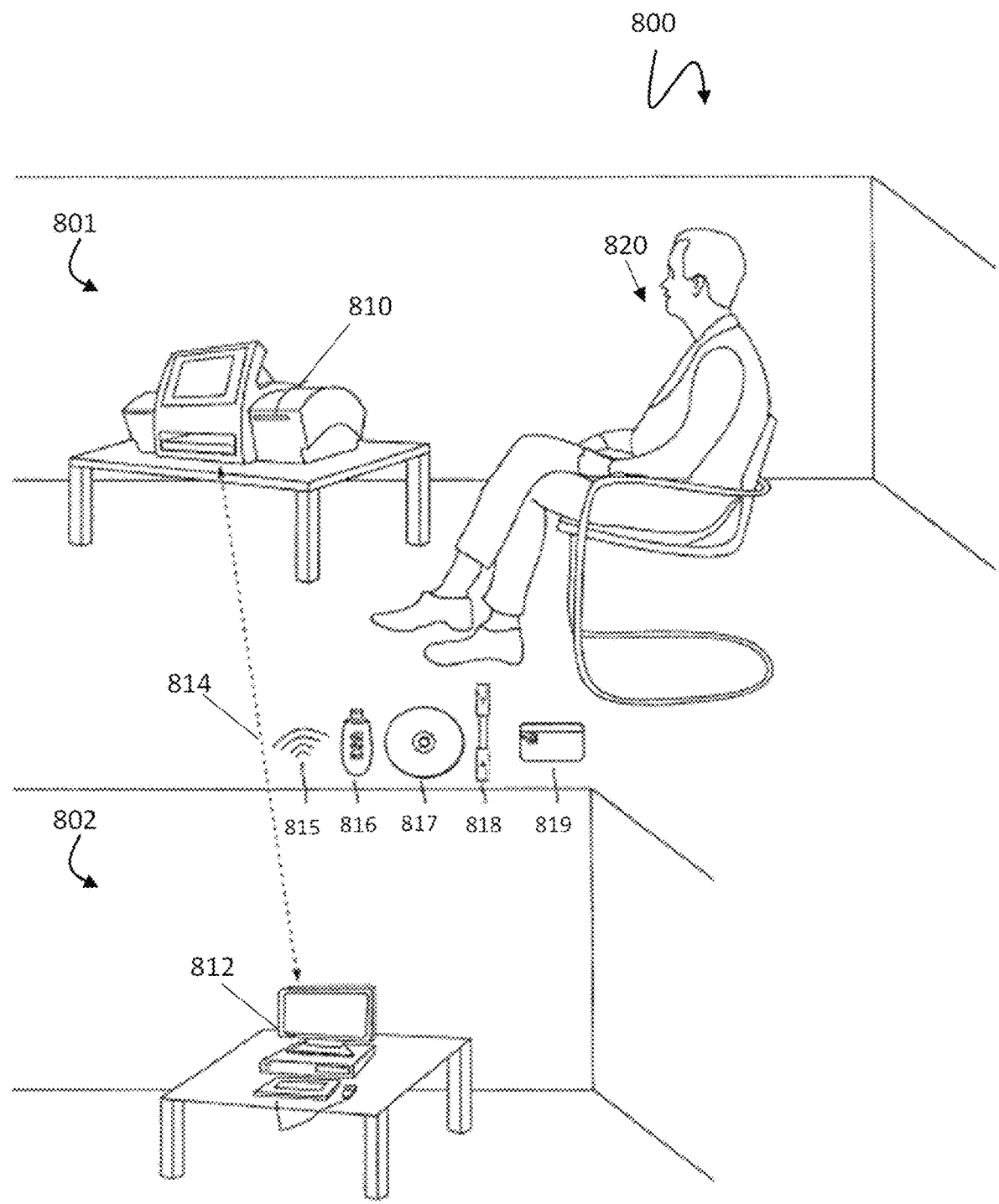
FIG. 8 is a schematic illustration showing an example implementation of an Empathy Garden according to the system described herein.

FIG. 8 is a schematic illustration showing an example implementation of an Empathy Garden system 800 according to the system described herein and that may be an implementation of the output system 216 described above. A presentation, display and/or information distribution device ("Empathy Garden device") 810 may be used for promulgating user experience information generated by a UX computing system component ("UX component") 812, that may be one or more components of the UX computing system 208 discussed herein, to an audience 820 of the Empathy Garden presentation. For example, the audience 820 may be internal product and service developers, engineers, designers, marketers etc. of the enterprise organization. As shown in the illustrated example, in an implementation, the Empathy Garden device 810 may be an example medical device having a controlled demonstration with which the audience 820 may interact; however, in other implementations, the Empathy Garden device 810 may be implemented in other ways, including in the form of computers, displays, exhibition devices, demonstration devices, and/or other types of experiential and interactive information communicating devices, as further discussed in detail below.

The Empathy Garden device 810 and the UX component 812 may exchange information, both before, during and after presentation of information to the audience 820. The Empathy Garden device 810 and the UX component 812 need not be situated close to one another. This is indicated by the different locations 801 and 802 in which the Empathy Garden device 810 and the UX component 812 may be located. The information used to generate the presentation experience of the Empathy Garden device 810 may be transmitted from the UX component 812 to the Empathy Garden device 810. This is indicated by a dotted double arrow 814. Moreover, in a further embodiment, data can also be transmitted from the Empathy Garden device 810 to the component 812, for example, to allow interactive exchanges in connection with the presentation in the Empathy Garden.

There are various implementations of data exchange between the devices 810 and 812 that may be provided for purposes of the display, presentation and/or distribution of processed user experience information in connection with the Empathy Garden presentation experience. The communication may include wireless data communication 815, for example, wireless local area network (WLAN), mobile wireless, BLUETOOTH, infrared or the like or similar non-hardwired communication methods. Other physically based communication, such as a portable rewritable memory medium 816 implemented as a universal serial bus (USB) USB stick and/or use of an optical memory medium 817 may be used. Additional possibilities of data transmission are represented by a network cable 818, which symbolizes hardwired communication such as location area network (LAN) or Internet communication and by a smartcard 819, for example a smartcard of the employee, equipped with at least one readable and writable nonvolatile memory (for example, EEPROM) and a data exchange mechanism, such as a magnetic strip, chip and/or a short range or near field communication (NFC) system. The data communication methods which are symbolized by the symbols 815 through 819 enable remote programming and information download to the Empathy Garden device 810 in connection with the interactive experience of the Empathy Garden. It will be appreciated that the various machine-implemented operations described herein may occur via the execution, by one or more respective processors, of processor-executable instructions stored on a tangible, non-transitory computer-readable medium, such as a random access memory (RAM), read-only memory (ROM), programmable read-only memory (PROM), and/or another electronic memory mechanism. Thus, for example, operations performed by any device described herein may be carried out according to instructions stored on and/or applications installed on the device, and via software and/or hardware of the device.

Figure 9:
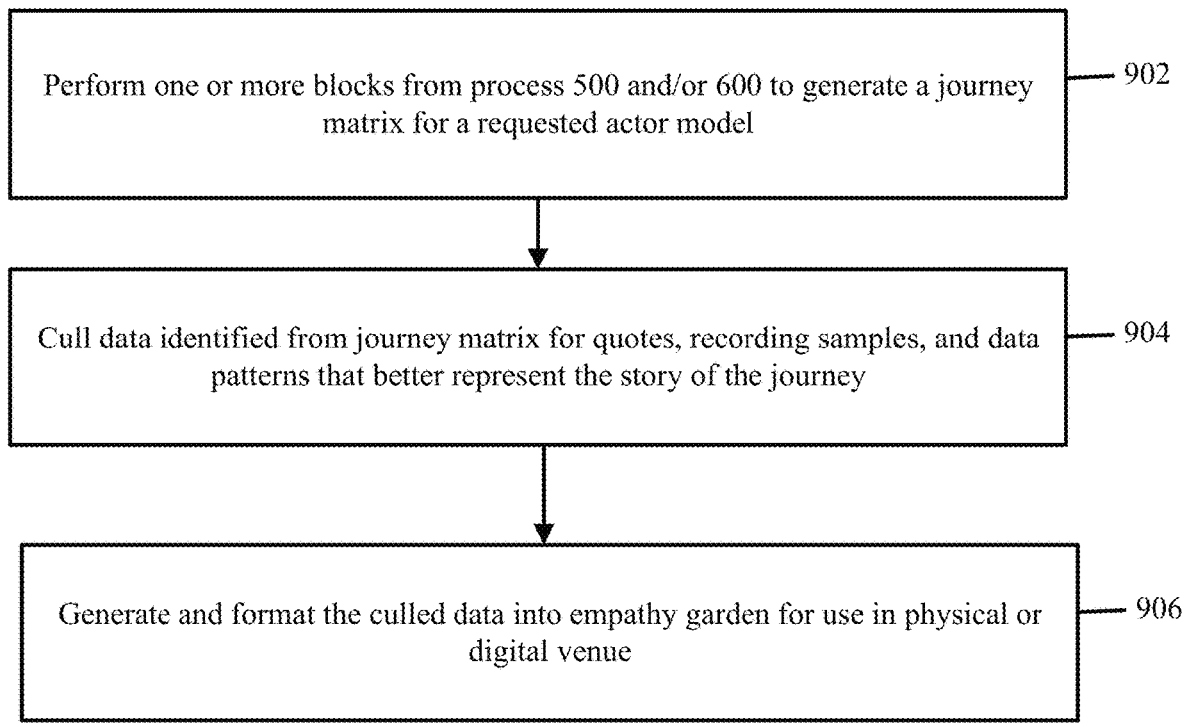
FIG. 9 is a flowchart of an exemplary process for generating an empathy garden in accordance with one or more examples of the present application.

FIG. 9 is a flowchart of an exemplary process for generating an empathy garden in accordance with one or more examples of the present application. The empathy garden may be an immersive form of data output. For instance, like a journey matrix, an empathy garden may tell a story of a population-of-interest's experience in a given context. In other words, it may describe the journey of a home patient's experiences throughout their history with dialysis. The empathy garden may be composed of first-hand recordings with actors, images collected during a research project (e.g., observation data), printed quotes taken directly from the actors, and/or the simulation of activities that may install a sense of empathy and understanding for the consumers of the material. In other words, the empathy garden may provide a more visceral and immersive means of experiencing the meaning behind the data discoveries.

In operation, at block 902, the UX computing system 208 may perform one or more blocks from process 500 and/or 600 to generate a journey matrix for a requested actor model. For example, the data from observation data (e.g., studies) may be entered into the user hub 210. A researcher may provide a request to the UX computing system 208 for an actor model. The persona farm 212 may query the normalized data and provide population patterns for the requested actor model. The journey matrix generator 214 may provide temporal analysis and generate a journey matrix for the requested actor model.

At block 904, the UX computing system 208 may cull data identified from the journey matrix for quotes, recording samples, and data patterns that better represent the story of the journey matrix. For example, the UX computing system 208 may analyze the actors and/or moments associated with journey matrix. The UX computing system 208 may further review the received observation data associated with these moments to identify potential quotes, recording samples, data patterns and so on.

At block 906, the UX computing system 208 may generate and format the culled data into an empathy garden for use in a physical or digital venue. For example, based on the analysis and review in block 904, the UX computing system 208 may generate an empathy garden that includes the quotes, recording samples, data patterns, and so on for these moments from the journey matrix. Afterwards, the UX computing system 208 may provide the empathy garden to a second device such as the output system 216.

In some instances, the UX computing system 208 may generate the empathy garden using operator input. For example, after generating the journey matrix, the UX computing system 208 may cause display of the journey matrix. Then, the UX computing system 208 may gather and/or retrieve data associated with one or more moments from the journey matrix based on operator input. For example, a researcher may seek to learn more about one or more moments (e.g., dialysis machine alarm going off) from the journey matrix and use the UX computing system 208 to review the data from the survey associated with these moments. The researcher may then use the UX computing system 208 to gather quotes, recording samples, and so on and insert them into an empathy garden.

An exemplary use of the UX computing system 208, including the user hub 210, the persona farm 212, and the journey matrix generator 214, is described below to generate actor models and/or journey matrices. However, it will be recognized that the below is merely an example, and the UX computing system 208 may generate actor models and/or journey matrices using various different methods, processes, and/or algorithms as described above.

In some instances, the user hub 210 of the UX computing system 208 may receive raw data input based on two separate layers (e.g., instances) of input—a configuration layer and a data entry layer. In the configuration layer, the user hub 210 may collect the meta-data required to render the study input forms for performing the studies. In the data entry layer, the user hub 210 may collect the data from the studies using the meta-data. In other words, the user hub 210 may display two different sets of UIs for these two layers and in some variations, two different user groups may input information into the user hub 210 using the two sets of UIs.

For example, a study administrator may input the study configuration (e.g., the meta-data for the study) for the configuration layer. For instance, the study administrator may be in charge of a department that may run a study on evaluating a new home peritoneal (PD) dialysis machine with at home PD patients. The user hub 210 may provide UIs to the study administrator such that the study administrator is able to upload the protocols and forms (e.g., meta-data) for the study. Additionally, and/or alternatively, the user hub 210 may further provide UIs to allow the study administrator to configure the data input forms for various types of data collected for each actor (e.g., participant) to be entered by a contributing researcher. After the study administrator has configured the study's data entry forms and/or additional meta-data in the user hub 210 and in the data entry layer, the user hub 210 may collect the participant data from one or more contributing researchers. For example, the user hub 210 may provide UIs such that the contributing researchers may input the participant data so that it may comply with the meta-data provided by the study administrator. The contributing researchers may enter the information that they collect for their study, per their protocol, into the forms that were specifically configured for their information. As such, the UX computing system 208 may have a complete description of the study's architecture (e.g., based on the meta-data from the study administrator), as well as the individual data points collected in the research (e.g., from the contributing researchers). Furthermore, because the data was stored in the system using common taxonomies and meta-data descriptions, the UX computing system 208 may analyze how the data from the different studies may relate to each other.

After using the user hub 210 to provide the data, the persona farm 212 of the UX computing system 208 may be used to investigate relevant actor clusters that the data renders (e.g., the UX computing system 208 may be able to build a persona for a particular research question). For instance, the UX computing system 208 may analyze the entered data from the studies (e.g., from the contributing researchers and/or the study administrators) and the data the UX computing system 208 has access to for those actors and similar actors from the different studies. Based on the analysis, the UX computing system 208 may determine the important aspects from the data (e.g., what bubbles to the surface). This may be done using the data from a single study or the data from multiple different studies. Further, each use of the persona farm 212 may be a kind of data query that gets rendered and associated with actors within (e.g., stored in) the UX computing system 208. The persona farm 212 may determine a mathematical representation of how the data within the UX computing system 208 relates to each other. Therefore, in configuring a query for the persona farm 212, the researcher may configure as many constraints (e.g., assumptions) as are appropriate for their research question. For example, a researcher may provide to the persona farm 212 a question such as what does a generic middle-aged male having a certain disease or taking a certain medication have for comorbidities and how does he feel about his dialysis experience. In such an example, the persona farm 212 may cluster the data along clinical values and/or the emotional profile of the moments that were entered for a journey study. In a less constrained query, a researcher may provide to the persona farm 212 a question such as "what are my user segments and what dimensions best define them, so I can modify my designs to fit those specific needs." Here, the researcher provides fewer assumptions to the persona farm 212 and the persona farm 212/UX computing system 208 may allow for a more free-reign to look for the data-driven clustering patterns.

In other words, the persona farm 212 may receive a query from the researcher that includes a configuration of "included" and "considered" parameters. The "included" parameters are the data sets that are to be clustered by the persona farm 212. The "considered" parameters are the constraints. Therefore, the persona farm 212 may include all known clinical data, as well as all moment aspects from a particular study, and constrain it by any dimension that the researcher would want (e.g., gender, age, modality, and so on). The constraints may be assumptions that the researcher is making based on what the researcher views as important and should be considered. The more considerations that are provided by the researcher to the persona farm 212, the tighter and potentially more biased the outcome.

After using the data-driven clustering patterns, the persona farm 212 may determine an actor model for each of the clusters. The actor model may be relevant to the context of the query from the researcher. For instance, the same body of actors may be clustered differently should the researcher frame their research question and constraints in a different way. The UX computing system 208 may generate an actor model, associate the actor model with the query (e.g., research question), and tag the contributing actor entries for association. In that way, the UX computing system 208 may present a researcher with what factors contributed to the actor model and the UX computing system 208 may allow the researcher to look back at the research that produced those patterns.

After generating the actor model, the journey matrix generator 214 may generate a journey matrix for the actor model. The journey matrix may include the actor model being investigated, common moments ordered by time, associated moment type data for each moment within the set. The data may then be rendered as a data visualization.

In some variations, the moment type data may be different depending on the study. In other words, each study may have a different moment type (e.g., set of data aspects associated with a line of inquiry). In one such example, a moment type may include aspects such as quote from interview, time when the moment within a story happened, people who were present during the event, feelings that were expressed for that moment (including associated research confidence levels for those scores), and the place where the moment occurred. After the moment type data is collected, the UX computing system 208 may cluster the moments together into categories and/or sub-categories for classification and/or labeling (e.g., clustering the moments into dialysis training moments, modality selection moments, and so on) as well as temporally (e.g., life before dialysis, life with dialysis, and life after dialysis).

To put it another way, in some examples, the UX computing system 208 may receive input from a study administrator for a particular study such as responses to a survey about dialysis from a patient and their experience throughout dialysis. The input may include meta-data such as configuration information indicating a particular actor (e.g., patient), demographics of the actor (e.g., age, gender, and so on), comorbidities of the actor, and/or one or more moment data type information (e.g., time, event, feeling (i.e., happy, sad)).

Based on the meta-data, the UX computing system 208 may provide one or more user interfaces for the contributing researchers to input their data. For instance, the contributing researchers may input a particular actor that participated in the study (e.g., a first patient undergoing dialysis), demographics of the actor (e.g., [age, 50], [gender, male], [comorbidities, continuous ambulatory peritoneal dialysis (CAPD)]), a first moment data type information (e.g., [time, 2020/7/1], [event, first standard dialysis session], [feeling, nervous]), a second moment data type information (e.g., [time, 2020/8/1], [event, second standard dialysis session], [feeling, neutral]), and a third moment data type information (e.g., [time, 2020/10/1], [event, completion of dialysis treatment], [feeling, excited]).

The UX computing system 208 may receive the data from the contributing researchers and store it within the user hub 210. Furthermore, the UX computing system 208 may parse through the data and include identifiers for the data to convert it into standardized form. For example, the UX computing system 208 may assign a story classification identifier for each particular actor undergoing dialysis treatment. In other words, each of the contributing researcher's input (e.g., the particular actor that participated in the study, the demographics of the actor, and the first, second, and third moment data type information) may be consolidated into a data element and assigned a story classification identifier. Furthermore, each of the first, second, and third moment data type information may further be assigned a moment classification identifier. For instance, the first moment data type information (e.g., [time, 2020/7/1], [event, first standard dialysis session], [feeling, nervous]) may be stored within the user hub 210 with a moment classification identifier.

After storing the information into the user hub 210, the UX computing system 208 may use the data to generate journey matrices, actor models, and/or empathy gardens. For example, a researcher may input a query into the UX computing system 208 that asks "what does a generic middle-aged male on CAPD have for comorbidities and how does he feel about his dialysis experience?" The UX computing system 208 may parse through the studies that have been input into the user hub 210 and provide an actor model that includes actors (e.g., the actor described in the preceding paragraphs) that meet the researcher's query. Additionally, and/or alternatively, the UX computing system 208 may generate a journey matrix for the actor model of the researcher's query based on the first, second, and third moment data type information. The journey matrix may indicate moments similar to the first, second, and third moment data type information described above.

All references, including publications, patent applications, and patents, cited herein are hereby incorporated by reference to the same extent as if each reference were individually and specifically indicated to be incorporated by reference and were set forth in its entirety herein.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present application covers further embodiments with any combination of features from different embodiments described above and below.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

The invention claimed is:

1. A method, comprising:
   receiving, by a user experience (UX) computing system, observation data in a plurality of non-standardized data formats, wherein the observation data comprises one or more surveys describing user experiences associated with a plurality of actors interacting with a product or service associated with an enterprise organization;
   converting, by the UX computing system, the observation data from the plurality of non-standardized data formats into one or more standardized data formats using a plurality of classification identifiers, wherein the plurality of classification identifiers comprises a section classification identifier associated with a plurality of section data elements, a story classification identifier associated with a plurality of story data elements, and a moment classification identifier associated with a plurality of moment data elements, wherein converting the observation data into the one or more standardized data formats comprises:
      breaking down the observation data into the plurality of section data elements, wherein the plurality of section data elements comprises a plurality of structured and unstructured section data elements;
      breaking down the plurality of unstructured section data elements into a plurality of first story data elements using artificial intelligence (AI) algorithms;
      breaking down the plurality of structured section data elements into a plurality of second story data elements without using AI algorithms, wherein the plurality of story data elements comprise the plurality of first story data elements and the plurality of second story data elements, and wherein each of the plurality of story data elements is associated with a user experience of an actor interacting with the product or service at a plurality of different instances in time; and
      breaking down each of the plurality of story data elements into the plurality of moment data elements, wherein each of the plurality of moment data elements is associated with a plurality of variables at a particular instance in time from the plurality of different instances in time;
   receiving, by the UX computing system, a request indicating a particular actor model, wherein the particular actor model represents a subset of the plurality of actors;
   generating, by the UX computing system, the particular actor model based on the request and the converted observation data, wherein generating the particular actor model is based on:
      determining a plurality of binary values from the converted observation data;

calculating an n-dimensional distance between the plurality of actors identified in the observation data based on the plurality of binary values; and clustering a subset of the plurality of actors together based on the request and using a clustering algorithm;

generating, by the UX computing system, a journey matrix for the particular actor model based on the converted observation data, wherein the journey matrix indicates a plurality of sequential moments describing a nephrologist throughout a dialysis treatment for a patient;

causing display of the journey matrix;

receiving, by the UX computing system, operator input indicating a request for original data associated with one or more moments from the journey matrix; and based on the operator input, providing, by the UX computing system, at least a portion of the one or more surveys from the observation data, wherein the portion of the one or more surveys comprises quotes or recording samples associated with the one or more moments from the journey matrix.

2. The method of claim 1, wherein converting the observation data into the one or more standardized data formats is based on using a user hub information architecture comprising the plurality of classification identifiers.

3. The method of claim 2, wherein converting the observation data into the one or more standardized data formats further comprises:

assigning a classification identifier from the plurality of classification identifiers at each stage of the break down of the observation data.

4. The method of claim 1, wherein breaking down the plurality of structured section data elements into the plurality of second story data elements is based on operator input associated with an operator.

5. The method of claim 1, wherein generating the journey matrix for the particular actor model based on the converted observation data comprises:

selecting, based on a taxonomy database, a subset of the plurality of moment data elements to include into the journey matrix, wherein the subset of the plurality of moment data elements is associated with the subset of the plurality of actors; and generating the journey matrix for the particular actor model by incorporating each of the subset of the plurality of moment data elements sequentially one after another based on an average temporal order for each of the subset of the plurality of moment data elements.

6. The method of claim 5, wherein selecting the subset of the plurality of moment data elements is based on operator input associated with an operator.

7. The method of claim 5, wherein the method further comprises:

categorizing the plurality of moment data elements into one or more categories of moments based on the taxonomy database, and wherein selecting the subset of the plurality of moment data elements is based on a number of the plurality of moment data elements within the one or more categories exceeding a threshold.

8. The method of claim 1, wherein the method further comprises:

generating an empathy garden based on the journey matrix, wherein the empathy garden comprises the journey matrix and information associated with a moment data element from the journey matrix; and providing the empathy garden and the journey matrix to a second device.

9. The method of claim 1, wherein the AI algorithms comprise one or more natural language processing AI algorithms.

10. A user experience (UX) computing system, comprising:

one or more processors; and a non-transitory computer-readable medium having processor-executable instructions stored thereon, wherein the processor-executable instructions, when executed by the one or more processors, facilitate:

receiving observation data in a plurality of non-standardized data formats, wherein the observation data comprises one or more surveys describing user experiences associated with a plurality of actors interacting with a product or service associated with an enterprise organization;

converting the observation data from the plurality of non-standardized data formats into one or more standardized data formats using a plurality of classification identifiers, wherein the plurality of classification identifiers comprises a section classification identifier associated with a plurality of section data elements, a story classification identifier associated with a plurality of story data elements, and a moment classification identifier associated with a plurality of moment data elements, wherein converting the observation data into the one or more standardized data formats comprises:

breaking down the observation data into the plurality of section data elements, wherein the plurality of section data elements comprises a plurality of structured and unstructured section data elements;

breaking down the plurality of unstructured section data elements into a plurality of first story data elements using artificial intelligence (AI) algorithms;

breaking down the plurality of structured section data elements into a plurality of second story data elements without using AI algorithms, wherein the plurality of story data elements comprises the plurality of first story data elements and the plurality of second story data elements, and wherein each of the plurality of story data elements is associated with a user experience of an actor interacting with the product or service at a plurality of different instances in time; and breaking down each of the plurality of story data elements into the plurality of moment data elements, wherein each of the plurality of moment data elements is associated with a plurality of variables at a particular instance in time from the plurality of different instances in time;

receiving a request indicating a particular actor model, wherein the particular actor model represents a subset of the plurality of actors;

generating the particular actor model based on the request and the converted observation data, wherein generating the particular actor model is based on:

determining a plurality of binary values from the converted observation data;

calculating an n-dimensional distance between the plurality of actors identified in the observation data based on the plurality of binary values; and clustering a subset of the plurality of actors together based on the request and using a clustering algorithm;

generating a journey matrix for the particular actor model based on the converted observation data, wherein the journey matrix indicates a plurality of sequential moments describing a nephrologist throughout a dialysis treatment for a patient;

causing display of the journey matrix;

receiving operator input indicating a request for original data associated with one or more moments from the journey matrix; and based on the operator input, providing at least a portion of the one or more surveys from the observation data, wherein the portion of the one or more surveys comprises quotes or recording samples associated with the one or more moments from the journey matrix.

11. The system of claim 10, wherein converting the observation data into the one or more standardized data formats is based on using a user hub information architecture comprising the plurality of classification identifiers.

12. The system of claim 11, wherein converting the observation data into one or more standardized data formats further comprises:

assigning a classification identifier from the plurality of classification identifiers at each stage of the break down of the observation data.

13. The system of claim 10, wherein the processor-execution instructions, when executed, further facilitate:

generating the particular actor model based on the request and the converted observation data, wherein generating the journey matrix is based on the generated actor model.

14. A non-transitory computer-readable medium having processor-executable instructions stored thereon, wherein the processor-executable instructions, when executed, facilitate:

receiving observation data in a plurality of non-standardized data formats, wherein the observation data comprises one or more surveys describing user experiences associated with a plurality of actors interacting with a product or service associated with an enterprise organization;

converting the observation data from the plurality of non-standardized data formats into one or more standardized data formats using a plurality of classification identifiers, wherein the plurality of classification identifiers comprises a section classification identifier associated with a plurality of section data elements, a story classification identifier associated with a plurality of story data elements, and a moment classification identifier associated with a plurality of moment data elements, wherein converting the observation data into the one or more standardized data formats comprises:

breaking down the observation data into the plurality of section data elements, wherein the plurality of section data elements comprises a plurality of structured and unstructured section data elements;

breaking down the plurality of unstructured section data elements into a plurality of first story data elements using artificial intelligence (AI) algorithms;

breaking down the plurality of structured section data elements into a plurality of second story data elements without using AI algorithms, wherein the plurality of story data elements comprises the plurality of first story data elements and the plurality of second story data elements, and wherein each of the plurality of story data elements is associated with a user experience of an actor interacting with the product or service at a plurality of different instances in time; and breaking down each of the plurality of story data elements into the plurality of moment data elements, wherein each of the plurality of moment data elements is associated with a plurality of variables at a particular instance in time from the plurality of different instances in time;

receiving a request indicating a particular actor model, wherein the particular actor model represents a subset of the plurality of actors;

generating the particular actor model based on the request and the converted observation data, wherein generating the particular actor model is based on:

determining a plurality of binary values from the converted observation data;

calculating an n-dimensional distance between the plurality of actors identified in the observation data based on the plurality of binary values; and clustering a subset of the plurality of actors together based on the request and using a clustering algorithm;

generating a journey matrix for the particular actor model based on the converted observation data, wherein the journey matrix indicates a plurality of sequential moments describing a nephrologist throughout a dialysis treatment for a patient;

causing display of the journey matrix;

receiving operator input indicating a request for original data associated with one or more moments from the journey matrix; and based on the operator input, providing at least a portion of the one or more surveys from the observation data, wherein the portion of the one or more surveys comprises quotes or recording samples associated with the one or more moments from the journey matrix.

* * * * *